(12) United States Patent
Zhao

(10) Patent No.: US 11,123,178 B2
(45) Date of Patent: Sep. 21, 2021

(54) POWER CALCULATOR FOR AN OPHTHALMIC APPARATUS WITH CORRECTIVE MERIDIANS HAVING EXTENDED TOLERANCE OR OPERATION BAND

(71) Applicant: Johnson & Johnson Surgical Vision, Inc., Santa Ana, CA (US)

(72) Inventor: Huawei Zhao, Saint Augustine, FL (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 153 days.

(21) Appl. No.: 15/467,372

(22) Filed: Mar. 23, 2017

(65) Prior Publication Data
US 2017/0273779 A1 Sep. 28, 2017

Related U.S. Application Data

(60) Provisional application No. 62/312,321, filed on Mar. 23, 2016, provisional application No. 62/312,338, (Continued)

(51) Int. Cl.
*A61F 2/16* (2006.01)
*G06F 30/20* (2020.01)
(Continued)

(52) U.S. Cl.
CPC .......... *A61F 2/1645* (2015.04); *A61B 3/0025* (2013.01); *A61F 2/1613* (2013.01); (Continued)

(58) Field of Classification Search
CPC ......... G06F 17/50; G02C 7/024; G02C 7/027; G02C 7/028; G02B 27/0012
See application file for complete search history.

(56) References Cited

U.S. PATENT DOCUMENTS

| | | | |
|---|---|---|---|
| 2,077,092 | A | 4/1937 | Broder |
| 3,305,294 | A | 2/1967 | Alvarez |
| | | (Continued) | |

FOREIGN PATENT DOCUMENTS

| | | | |
|---|---|---|---|
| CN | 1035363 A | 9/1989 | |
| CN | 1039487 A | 2/1990 | |
| | (Continued) | | |

OTHER PUBLICATIONS

Hill W., Potvin R., "Monte Carlo simulation of expected outcomes with the AcrySof® toric intraocular lens", BMC Ophthalmology 2008; 8:22. doi: 10.1186/1471-2415-8-22. (Year: 2008).*
(Continued)

*Primary Examiner* — Omar F Fernandez Rivas
*Assistant Examiner* — David A Hopkins
(74) *Attorney, Agent, or Firm* — Johnson & Johnson Surgical Vision, Inc.

(57) ABSTRACT

An IOL calculator is disclosed to determine the spherical equivalent (SE) and cylinder power for toric lenses and ophthalmic apparatuses having the extended band of operational meridian, such as the rotational extended tolerant toric intraocular lens. The IOL calculator may also be used for an extended rotational tolerant toric intraocular lens, an extended depth of field intraocular lens, an extended depth of field toric intraocular lens, an extended range of vision intraocular lens, and an extended range of vision toric intraocular lens.

11 Claims, 19 Drawing Sheets

Related U.S. Application Data filed on Mar. 23, 2016, provisional application No. 62/363,428, filed on Jul. 18, 2016.

(51) Int. Cl.

| | | |
|---|---|---|
| *G02B 27/00* | (2006.01) | |
| *A61B 3/00* | (2006.01) | |
| *G02C 7/00* | (2006.01) | |
| *G02C 7/04* | (2006.01) | |
| *G06F 30/00* | (2020.01) | |
| *G06F 7/548* | (2006.01) | |
| *G02C 7/06* | (2006.01) | |
| *A61B 3/036* | (2006.01) | |

(52) U.S. Cl.
CPC .......... *A61F 2/1624* (2013.01); *A61F 2/1654* (2013.01); *G02B 27/0012* (2013.01); *G02C 7/00* (2013.01); *G02C 7/042* (2013.01); *G02C 7/06* (2013.01); *G06F 7/548* (2013.01); *G06F 30/00* (2020.01); *G06F 30/20* (2020.01); *A61B 3/036* (2013.01); *G02B 27/0075* (2013.01); *G02C 2202/02* (2013.01); *G02C 2202/10* (2013.01); *G02C 2202/20* (2013.01); *G02C 2202/22* (2013.01)

(56) References Cited

U.S. PATENT DOCUMENTS

| | | |
|---|---|---|
| 3,367,734 A | 2/1968 | Karl |
| 3,735,685 A | 5/1973 | Plummer |
| 4,010,496 A | 3/1977 | Neefe |
| 4,056,311 A | 11/1977 | Winthrop et al. |
| 4,162,122 A | 7/1979 | Cohen |
| 4,210,391 A | 7/1980 | Cohen et al. |
| 4,319,564 A | 3/1982 | Karickhoff |
| 4,338,005 A | 7/1982 | Cohen |
| 4,340,283 A | 7/1982 | Cohen et al. |
| 4,370,760 A | 2/1983 | Kelman |
| 4,377,873 A | 3/1983 | Reichert |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,593,981 A | 6/1986 | Scilipoti |
| 4,605,409 A | 8/1986 | Kelman |
| 4,605,411 A | 8/1986 | Fedorov |
| 4,629,460 A | 12/1986 | Dyer |
| 4,629,462 A | 12/1986 | Feaster |
| 4,636,049 A | 1/1987 | Blaker |
| 4,637,697 A | 1/1987 | Freeman |
| 4,642,112 A | 2/1987 | Freeman |
| 4,655,565 A | 4/1987 | Freeman |
| 4,673,406 A | 6/1987 | Schlegel |
| 4,676,791 A | 6/1987 | Lemaster |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,734,095 A | 3/1988 | Siepser |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,539 A | 9/1989 | Lee |
| 4,898,461 A | 2/1990 | Portney |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,114,220 A | 5/1992 | Baude |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,173,723 A | 12/1992 | Volk et al. |
| 5,184,405 A | 2/1993 | Cress |
| 5,197,981 A | 3/1993 | Southard |
| 5,201,763 A | 4/1993 | Brady et al. |
| 5,203,790 A | 4/1993 | McDonald |
| 5,217,491 A | 6/1993 | Vanderbilt |
| 5,225,858 A | 7/1993 | Portney |
| 5,225,997 A | 7/1993 | Lederer et al. |
| 5,229,797 A | 7/1993 | Futhey et al. |
| 5,258,025 A | 11/1993 | Fedorov et al. |
| 5,278,592 A | 1/1994 | Marie et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,567,365 A | 10/1996 | Weinschenk, III et al. |
| 5,571,177 A | 11/1996 | Deacon et al. |
| 5,620,720 A | 4/1997 | Glick et al. |
| 5,628,796 A | 5/1997 | Suzuki |
| 5,652,638 A | 7/1997 | Roffman et al. |
| 5,691,800 A | 11/1997 | Iki et al. |
| 5,699,142 A | 12/1997 | Lee et al. |
| 5,716,403 A | 2/1998 | Tran et al. |
| 5,748,282 A | 5/1998 | Freeman |
| 5,760,871 A | 6/1998 | Kosoburd et al. |
| 5,796,462 A | 8/1998 | Roffman et al. |
| 5,801,807 A | 9/1998 | Satake et al. |
| 5,928,282 A | 7/1999 | Nigam |
| 5,968,094 A | 10/1999 | Werblin et al. |
| 6,015,435 A | 1/2000 | Valunin et al. |
| 6,051,024 A | 4/2000 | Cumming |
| 6,055,111 A | 4/2000 | Nomura et al. |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,179,870 B1 | 1/2001 | Sourdille et al. |
| 6,210,005 B1 | 4/2001 | Portney |
| 6,235,055 B1 | 5/2001 | Chu |
| 6,261,321 B1 | 7/2001 | Kellan |
| 6,286,956 B1 | 9/2001 | Oyama et al. |
| 6,319,282 B1 | 11/2001 | Nishi |
| 6,338,559 B1 | 1/2002 | Williams et al. |
| 6,419,697 B1 | 7/2002 | Kelman |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |

(56) References Cited

U.S. PATENT DOCUMENTS

| | | |
|---|---|---|
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |
| 6,598,606 B2 | 7/2003 | Terwee et al. |
| 6,609,793 B2 | 8/2003 | Norrby et al. |
| 6,705,729 B2 | 3/2004 | Piers et al. |
| 6,709,102 B2 | 3/2004 | Duppstadt |
| 6,802,605 B2 | 10/2004 | Cox et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,425,068 B2 | 9/2008 | Koest |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,615,073 B2 | 11/2009 | Deacon et al. |
| 7,616,330 B2 | 11/2009 | Neal et al. |
| 7,713,299 B2 | 5/2010 | Brady et al. |
| 7,794,497 B2 | 9/2010 | Brady et al. |
| 7,857,451 B2 | 12/2010 | Thibos et al. |
| 7,871,162 B2 | 1/2011 | Weeber |
| 7,879,089 B2 * | 2/2011 | Hong .................... A61F 2/1637 623/6.11 |
| 7,993,398 B2 | 8/2011 | Deacon et al. |
| 8,241,354 B2 | 8/2012 | Hong et al. |
| 8,740,382 B1 | 6/2014 | Liu et al. |
| 8,764,822 B2 * | 7/2014 | Harris .................... G02C 7/028 623/5.11 |
| 8,862,447 B2 * | 10/2014 | Weeber .................... A61F 2/16 703/6 |
| 9,216,080 B2 * | 12/2015 | Bogaert ................ A61F 2/1645 |
| 9,241,627 B2 | 1/2016 | Steinmueller |
| 9,393,108 B2 | 7/2016 | Canovas et al. |
| 9,491,431 B2 | 11/2016 | Zhou |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0021824 A1 | 2/2004 | Ye et al. |
| 2004/0021825 A1 | 2/2004 | Richardson |
| 2004/0054358 A1 | 3/2004 | Cox et al. |
| 2004/0068317 A1 | 4/2004 | Knight |
| 2004/0080710 A1 | 4/2004 | Wooley et al. |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0150790 A1 | 8/2004 | Roffman et al. |
| 2004/0156014 A1 | 8/2004 | Piers et al. |
| 2004/0167622 A1 | 8/2004 | Sunalp et al. |
| 2005/0096226 A1 | 5/2005 | Stock et al. |
| 2005/0122474 A1 | 6/2005 | Koretz |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0055877 A1 | 3/2006 | Yanari |
| 2006/0066808 A1 | 3/2006 | Blum et al. |
| 2006/0068453 A1 | 3/2006 | Altieri |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0238702 A1 | 10/2006 | Glick et al. |
| 2006/0244904 A1 | 11/2006 | Hong et al. |
| 2006/0244916 A1 | 11/2006 | Guillon |
| 2006/0279700 A1 | 12/2006 | Liang |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 * | 11/2007 | Hong .................... A61F 2/141 351/159.74 |
| 2008/0018910 A1 | 1/2008 | Neal et al. |
| 2008/0030677 A1 | 2/2008 | Simpson |
| 2008/0161914 A1 | 7/2008 | Brady et al. |
| 2008/0231809 A1 | 9/2008 | Haigis |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0051876 A1 | 2/2009 | Seiler et al. |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0210054 A1 | 8/2009 | Weeber et al. |
| 2009/0234448 A1 | 9/2009 | Weeber et al. |
| 2009/0275929 A1 | 11/2009 | Zickler |
| 2009/0279048 A1 | 11/2009 | Hong et al. |
| 2009/0303465 A1 | 12/2009 | Clements et al. |
| 2009/0323020 A1 | 12/2009 | Zhao et al. |
| 2010/0016965 A1 | 1/2010 | Hong et al. |
| 2010/0082017 A1 | 4/2010 | Zickler et al. |
| 2010/0161048 A1 | 6/2010 | Schaper, Jr. |
| 2010/0220185 A1 | 9/2010 | Vertoprakhov et al. |
| 2010/0274234 A1 | 10/2010 | Liang |
| 2010/0315589 A1 | 12/2010 | Portney |
| 2011/0166652 A1 | 7/2011 | Bogaert et al. |
| 2011/0205486 A1 | 8/2011 | Zhao |
| 2012/0140166 A1 | 6/2012 | Zhao |
| 2012/0147321 A1 * | 6/2012 | Portney ................ A61F 2/1645 351/159.15 |
| 2012/0249955 A1 | 10/2012 | Sarver et al. |
| 2012/0310337 A1 * | 12/2012 | Hacker ................ A61B 3/0025 623/6.11 |
| 2012/0320334 A1 | 12/2012 | Ho et al. |
| 2013/0050637 A1 | 2/2013 | Roffman et al. |
| 2013/0307965 A1 | 11/2013 | Widman et al. |
| 2014/0016088 A1 | 1/2014 | De Rossi et al. |
| 2014/0135919 A1 | 5/2014 | Gontijo et al. |
| 2014/0160436 A1 | 6/2014 | Kasthurirangan et al. |
| 2014/0268042 A1 | 9/2014 | Bor et al. |
| 2014/0293426 A1 | 10/2014 | Dobschal |
| 2015/0062529 A1 | 3/2015 | Kasthurirangan et al. |
| 2015/0138350 A1 | 5/2015 | Videcoq |
| 2015/0250583 A1 | 9/2015 | Rosen et al. |
| 2015/0320547 A1 * | 11/2015 | Rosen .................. A61F 2/1613 623/6.23 |
| 2015/0359625 A1 | 12/2015 | Argal et al. |
| 2015/0362746 A1 | 12/2015 | Skudder et al. |
| 2016/0157997 A1 | 6/2016 | Gerlach et al. |

(56) References Cited

U.S. PATENT DOCUMENTS

| | | | |
|---|---|---|---|
| 2016/0299355 A1 | 10/2016 | Biemold et al. | |
| 2019/0243162 A1* | 8/2019 | Frison | A61F 2/1645 |

FOREIGN PATENT DOCUMENTS

| | | | |
|---|---|---|---|
| CN | 1406120 A | 3/2003 | |
| CN | 1833192 A | 9/2006 | |
| CN | 102099729 A | 6/2011 | |
| DE | 8107675 U1 | 7/1981 | |
| DE | 3439551 A1 | 4/1986 | |
| DE | 102005022683 A1 | 11/2006 | |
| EP | 226400 A2 | 6/1987 | |
| EP | 227357 A2 | 7/1987 | |
| EP | 0343067 A1 | 11/1989 | |
| EP | 0457553 A2 | 11/1991 | |
| EP | 681198 A1 | 11/1995 | |
| EP | 0926531 A1 | 6/1999 | |
| EP | 949529 A2 | 10/1999 | |
| EP | 957331 A2 | 11/1999 | |
| EP | 1424049 A1 | 6/2004 | |
| EP | 1310267 B1 | 1/2008 | |
| EP | 1424049 B1 | 6/2009 | |
| EP | 2182891 B1 | 4/2014 | |
| FR | 2745711 A1 | 9/1997 | |
| JP | H0255314 A | 2/1990 | |
| WO | 8603961 A1 | 7/1986 | |
| WO | 9109336 A1 | 6/1991 | |
| WO | 9222264 A1 | 12/1992 | |
| WO | 9303409 A1 | 2/1993 | |
| WO | 9507487 A1 | 3/1995 | |
| WO | 9856315 A1 | 12/1998 | |
| WO | 9905499 A1 | 2/1999 | |
| WO | 0019906 A1 | 4/2000 | |
| WO | 0111418 A1 | 2/2001 | |
| WO | 0135868 A1 | 5/2001 | |
| WO | 0154569 A1 | 8/2001 | |
| WO | 0163344 A1 | 8/2001 | |
| WO | 0182839 A1 | 11/2001 | |
| WO | 0189424 A1 | 11/2001 | |
| WO | 0221194 A2 | 3/2002 | |
| WO | 03009053 A1 | 1/2003 | |
| WO | 2004034129 A1 | 4/2004 | |
| WO | 2004090611 A2 | 10/2004 | |
| WO | 2004096014 A2 | 11/2004 | |
| WO | 05019906 A1 | 3/2005 | |
| WO | 06025726 A1 | 3/2006 | |
| WO | 2006032263 A2 | 3/2006 | |
| WO | 2006047698 A1 | 5/2006 | |
| WO | 06060477 A2 | 6/2006 | |
| WO | 2006060480 A2 | 6/2006 | |
| WO | 2007067872 A2 | 6/2007 | |
| WO | 2007092948 A1 | 8/2007 | |
| WO | 2007133384 A2 | 11/2007 | |
| WO | 2008045847 A2 | 4/2008 | |
| WO | 2008083283 A2 | 7/2008 | |
| WO | 2009020963 A1 | 2/2009 | |
| WO | 2009029515 A1 | 3/2009 | |
| WO | 2009076670 A1 | 6/2009 | |
| WO | 2009105567 A1 | 8/2009 | |
| WO | 2009137491 A1 | 11/2009 | |
| WO | 2010009254 A1 | 1/2010 | |
| WO | 2010009257 A1 | 1/2010 | |
| WO | 2012083143 A1 | 6/2012 | |
| WO | 2012085917 A1 | 6/2012 | |
| WO | WO-2012083143 A1 * | 6/2012 | A61F 2/1654 |
| WO | WO-2012154597 A1 * | 11/2012 | A61F 2/1637 |
| WO | 2015022215 A1 | 2/2015 | |
| WO | 2016123167 A1 | 8/2016 | |

OTHER PUBLICATIONS

Rita Mencucci et al., Clinical outcomes and rotational stability of a 4-haptic toric intraocular lens in myopic eyes, Journal of Cataract & Refractive Surgery, vol. 40, Issue 9, 2014, pp. 1479-1487, ISSN 0886-3350, https://doi.org/10.1016/j.jcrs.2 (Year: 2014).*

Herven Abelman and Shirley Abelman, "Tolerance and Nature of Residual Refraction in Symmetric Power Space as Principal Lens Powers and Meridians Change," Computational and Mathematical Methods in Medicine, vol. 2014, Article ID 492383, 8 pages, 2014. https://doi.org/10.1155/2014/492383. (Year: 2014).*

Narváez, Julio, et al. "Accuracy of intraocular lens power prediction using the Hoffer Q, Holladay 1, Holladay 2, and SRK/T formulas." Journal of Cataracts Refractive Surgery32.12 (2006): 2050-2053. (Year: 2006).*

Gobin, Laure, Marie-José Tassignon, and Danny Mathysen. "Spherotoric bag-in-the-lens intraocular lens: Power calculation and predictive misalignment nomogram." Journal of Cataract & Refractive Surgery 37.6 (2011): 1020-1030. (Year: 2011).*

Einighammer, Jens, et al. "The individual virtual eye: a computer model for advanced intraocular lens calculation." Journal of optometry 2.2 (2009): 70-82. (Year: 2009).*

Patel, Sudi, Larysa Tutchenko, and Oleksiy Voytsekhivskyy. "An Evaluation of Unexpected Refractive Outcomes Following Toric IOL Implantation for Astigmatism: A Sector Subtraction Graphical Method for Calculating the Effective Astigmatic Correction.", 2016, ResearchGate (Year: 2016).*

Næser, Kristian. "Assessment and statistics of surgically induced astigmatism." Acta ophthalmologies 86.thesis1 (2008): 1-28. (Year : 2008).*

Roach et al., "Toric IOLs: Four Options for Addressing Residual Astigmatism", EyeNet Magazine, accessed online at American Academy of Ophthalmology, Apr. 2012 (Year: 2012).*

Alpins, Noel, James KY Ong, and George Stamatelatos. "Refractive surprise after toric intraocular lens implantation: graph analysis." Journal of Cataract & Refractive Surgery 40.2 (2014): 283-294. (Year: 2014).*

Tseng, Santos S., and Joseph JK Ma. "Calculating the optimal rotation of a misaligned toric intraocular lens." Journal of Cataract & Refractive Surgery 34.10 (2008): 1767-1772. (Year: 2008).*

Ma, Joseph JK, and Santos S. Tseng. "Simple method for accurate alignment in toric phakic and aphakic intraocular lens implantation." Journal of Cataract & Refractive Surgery 34.10 (2008): 1631-1636. (Year: 2008).*

Savini, Giacomo, et al. "Influence of intraocular lens haptic design on refractive error." Journal of Cataract & Refractive Surgery 40.9 (2014): 1473-1478. (Year: 2014).*

Wisse, Robert PL, et al. "Validation of an Independent Web-Based Tool for Measuring Visual Acuity and Refractive Error (the Manifest versus Online Refractive Evaluation Trial): Prospective Open-Label Noninferiority Clinical Trial." Journal of medical Internet research 21.11 (2019): e14808. (Year: 2019).*

Orr, Peggy R., et al. "Manifest refraction versus autorefraction for patients with subfoveal choroidal neovascularization." Investigative ophthalmology & visual science 42.2 (2001): 447-452. (Year: 2001).*

Bonfadini, Gustavo, et al. "Optimization of intraocular lens constant improves refractive outcomes in combined endothelial keratoplasty and cataract surgery." Ophthalmology 120.2 (2013): 234-239. (Year: 2013).*

3D Flow, accessed via the website for 3D flow, Overview page (Year: 2020).*

Canovas, Carmen, and Pablo Artal. "Customized eye models for determining optimized intraocular lenses power." Biomedical optics express 2.6 (2011): 1649-1662. (Year: 2011).*

Covert, Douglas J., Christopher R. Henry, and Steven B. Koenig. "Intraocular lens power selection in the second eye of patients undergoing bilateral, sequential cataract extraction." Ophthalmology 117.1 (2010): 49-54. (Year: 2010).*

Eom, Youngsub, et al. "Use of corneal power-specific constants to improve the accuracy of the SRK/T formula." Ophthalmology 120.3 (2013): 477-481. (Year: 2013).*

Hong, Xin, and Xiaoxiao Zhang. "Optimizing distance image quality of an aspheric multifocal intraocular lens using a comprehensive statistical design approach." Optics Express 16.25 (2008): 20920-20934. (Year: 2008).*

(56) References Cited

OTHER PUBLICATIONS

Huang, David, et al. "Optical coherence tomography-based corneal power measurement and intraocular lens power calculation following laser vision correction (an American Ophthalmological Society thesis)." Transactions of the American Ophthalmological Society 111 (2013): 34. (Year: 2013).*
Latkany, Robert A., et al. "Intraocular lens calculations after refractive surgery." Journal of Cataract & Refractive Surgery 31.3 (2005): 562-570. (Year: 2005).*
Olsen, Thomas, and Peter Hoffmann. "C constant: new concept for ray tracing-assisted intraocular lens power calculation." Journal of Cataract & Refractive Surgery 40.5 (2014): 764-773. (Year: 2014).*
Packer, Mark. "Enhancements after premium IOL cataract surgery: tips, tricks, and outcomes." Current Ophthalmology Reports 2.1 (2014): 34-40. (Year: 2014).*
Retzlaff, John A., Donald R. Sanders, and Manus C. Kraff. "Development of the SRK/T intraocular lens implant power calculation formula." Journal of Cataract & Refractive Surgery 16.3 (1990): 333-340. (Year: 1990).*
Schuster, Alexander K., et al. "Intraocular lens calculation adjustment after laser refractive surgery using Scheimpflug imaging." Journal of Cataract & Refractive Surgery 42.2 (2016): 226-231. (Year: 2016).*
Tang, Maolong, et al. "Intraocular lens power calculation after previous myopic laser vision correction based on corneal power measured by Fourier-domain optical coherence tomography." Journal of Cataract & Refractive Surgery 38.4 (2012): 589-594. (Year: 2012).*
Fam, Han Bor, and Kooi Ling Lim. "Meridional analysis for calculating the expected spherocylindrical refraction in eyes with toric intraocular lenses." Journal of Cataract & Refractive Surgery 33.12 (2007): 2072-2076. (Year: 2007).*
Bacherneg, Alexander, et al. "Rotational stability and visual outcome after implantation of a new toric intraocular lens for the correction of corneal astigmatism during cataract surgery." Journal of Cataract & Refractive Surgery 39.9 (2013): 1390-1398. (Year: 2013).*
Krall, Eva M., et al. "Vector analysis of astigmatism correction after toric intraocular lens implantation." Journal of Cataract & Refractive Surgery 41.4 (2015): 790-799. (Year: 2015).*
International Search Report and Written Opinion for Application No. PCT/US2018/023946, dated Jun. 12, 2018, 16 pages.
Abelman H., et al. "Tolerance and Nature of Residual Refraction in Symmetric Power Space as Principal Lens Powers and Meridians Change," Computational and Mathematical Methods in Medicine, 2014, vol. 2014, pp. 1-12.
Baumeister M., et al., "Tilt and Decentration of Spherical and Aspheric Intraocular Lenses: Effect on Higher-Order Aberrations," Journal of Cataract & Refractive Surgery, 2009, vol. 35 (6), pp. 1006-1012.
Brown W.L., "Revisions to Tolerances in Cylinder Axis and in Progressive Addition Lens Power in ANSI Z80.1-2005," Optometry, 2006, vol. 77 (7), pp. 343-349.
Canovas C., et al., "Customized Eye Models for Determining Optimized Intraocular Lenses Power," Biomedical Optics Express, Jun. 1, 2011, vol. 2 (6), pp. 1649-1662.
International Search Report and Written Opinion for Application No. PCT/US2017/023772, dated Jul. 21, 2017, 14 pages.
International Search Report and Written Opinion for Application No. PCT/US2017/023864, dated Jul. 6, 2017, 15 pages.
International Search Report and Written Opinion for Application No. PCT/US2017/023888, dated Jul. 24, 2017, 14 pages.
International Search Report and Written Opinion for Application No. PCT/US2017/023897, dated Jul. 11, 2017, 17 pages.
Olsen T., "Simple Method to Calculate the Surgically Induced Refractive Change," Journal of Cataract & Refractive Surgery, Mar. 1993, vol. 19 (2), pp. 319-320.
International Search Report and Written Opinion for Application No. PCT/US2017/023836, dated Jun. 19, 2017, 12 pages.

Alfonso J.F., et al., "Prospective Study of the Acri.LISA Bifocal Intraocular Lens," Journal of Cataract Refractive Surgery, Nov. 2007, vol. 33 (11), pp. 1930-1935.
Alio J.L., et al., "Phakic Anterior Chamber Lenses for the Correction of Myopia: A 7-Year Cumulative Analysis of Complications in 263 Cases," Ophthalmology, Mar. 1999, vol. 106 (3), pp. 458-466.
Apple D.J., et al., "Anterior Chamber Lenses Part 1: Complications and Pathology and a Review of Designs," Journal of Cataract Refractive Surgery, Mar. 1987, vol. 13 (2), pp. 157-174.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.
Baikoff G., et al., "Angle-fixated Anterior Chamber Phakic Intraocular Lens for Myopia 7 to -19 Diopters," Journal of Refractive Surgery, May-Jun. 1998, vol. 14 (3), pp. 282-292.
Canovas C., et al., "Hybrid Adaptive-Optics Visual Simulator," Optical Letters, Jan. 15, 2010, vol. 35 (2), pp. 196-198.
Cheng X., et al., "Predicting Subjective Judgment of Best Focus with Objective Image Quality Metrics," Journal of Vision, Apr. 2004, vol. 4 (4), pp. 310-321.
CILCO Advertisement Brochure, Oct. 1982, 3 pages.
Cohen A.L., "Practical Design of a Bifocal Hologram Contact Lens or Intraocular Lens," Applied Optics, Jul. 1, 1992, vol. 31 (19), pp. 3750-3754.
De Almeida M.S., et al., "Different Schematic Eyes and their Accuracy to the in Vivo Eye: A Quantitative Comparison Study," Brazilian Journal of Physics, Jun. 2007, vol. 37 (2A), 10 pages.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
Egger J.R., "Use of Fresnel Lenses in Optical Systems: Some Advantages and Limitations," in: Atomic and Molecular Spectroscopy, vol. 193, Paul R. Yoder, Jr., ed., SPIE Proceedings, the International Society for Optical Engineering, 1979, pp. 63-69.
Farberov, "Manufacturing Fresnel Lenses for Cameras," Soviet Journal of Optical Technology, 1983, vol. 50 (3), pp. 186-188.
Gupta P.A., "Theoretical Analysis of the Fresnel lens as a Function of Design Parameters," Applied Energy, 1981, vol. 9 (4), pp. 301-310.
Kim J.H., et al., "The Analysis of Predicted Capsular Bag Diameter using Modified Model of Capsule Measuring Ring in Asians," Clinical and Experimental Ophthalmology, Apr. 2008, vol. 36 (3), pp. 238-244.
Liou H.L., et al., "Anatomically Accurate, Finite Model Eye for Optical Modeling," Journal of Optical Society of America, Aug. 1997, vol. 14 (8), pp. 1684-1695.
Liou H.L., et al., "The Prediction of Spherical Aberration with Schematic Eyes," Ophthalmic and Physiological Optics, Jan. 1996, vol. 16 (4), pp. 348-354.
Marinho A., "Results are Encouraging for Phakic IOLs, but More Work is needed," Refractive Surgery, Feb. 2000, p. 12, 15.
Marsack J.D., et al., "Metrics of Optical Quality Derived from Wave Aberrations Predict Visual Performance," Journal of Vision, Apr. 2004, vol. 4 (4), pp. 322-328.
Menapace R., "The Capsular Tension Rings," Journal of Cataract & Refractive Surgery, Dec. 10, 2008, Chap. 3, pp. 27-44.
Monsoriu J.A., et al., "Devil's Lenses," Optics Express, Oct. 17, 2007, vol. 15 (21), pp. 13858-13864.
Navarro R., et al., "Accommodation-Dependent Model of the Human Eye with Aspherics," Journal of the Optical Society of America, Aug. 1985, vol. 2 (8), pp. 1273-1281.
Nio Y.K., et al., "Effect of Intraocular Lens Implantation on Visual Acuity, Contrast Sensitivity, and Depth of Focus," Journal of Cataract and Refractive Surgery, Nov. 2003, vol. 29 (11), pp. 2073-2081.

(56) References Cited

OTHER PUBLICATIONS

Norrby S., et al., "Model Eyes for Evaluation of Intraocular Lenses," Applied Optics, Sep. 7, 2007, vol. 46 (26), pp. 6595-6605.

Piers P.A., et al., "Eye Models for the Prediction of Contrast Vision in Patients with New Intraocular Lens Designs," Optics Letters, Apr. 1, 2004, vol. 29 (7), pp. 733-735.

Piers P.A., et al., "Theoretical Comparison of Aberration-Correcting Customized and Aspheric Intraocular Lenses," Journal of Refractive Surgery, Apr. 2007, vol. 23 (4), pp. 374-384.

Praeger D.L., "Praeger Technique for the Insertion of the Copeland Radial IOL Posterior Chamber Placement," Copeland Lens, 1982, 7 pages.

Siedlecki D., et al., "Radial Gradient index Intraocular Lens: a Theoretical Model," Journal of Modern Optics, Feb. 20-Mar. 10, 2008, vol. 55 (4-5), pp. 639-647.

Strenn K., et al., "Capsular bag Shrinkage after Implantation of an Open-Loop Silicone Lens and a Poly(methyl methacrylate) Capsule Tension Ring," Journal of Cataract and Refractive Surgery, Dec. 1997, vol. 23 (10), pp. 1543-1547.

Tehrani M., et al., "Capsule Measuring Ring to Predict Capsular Bag Diameter and Follow its Course after Foldable Intraocular Lens Implantation," Journal of Cataract Refractive Surgery, Nov. 2003, vol. 29 (11), pp. 2127-2134.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Van Den Berg T.J., "Analysis of Intraocular Straylight, Especially in Relation to Age," Optometry and Vision Science, Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Vanderwerf D., et al., "Approximating the Fresnel Lens," Electro Optical Systems Design, 1982, pp. 47-52.

Vass C., et al., "Prediction of Pseudophakic Capsular bag Diameter based on Biometric Variables," Journal of Cataract and Refractive Surgery, Oct. 1999, vol. 25 (10), pp. 1376-1381.

Villegas E.A., et al., "Correlation between Optical and Psychophy, Sical Parameters as a Function of Defocus," Optometry and Vision Science, Jan. 1, 2002, vol. 79 (1), pp. 60-67.

\* cited by examiner

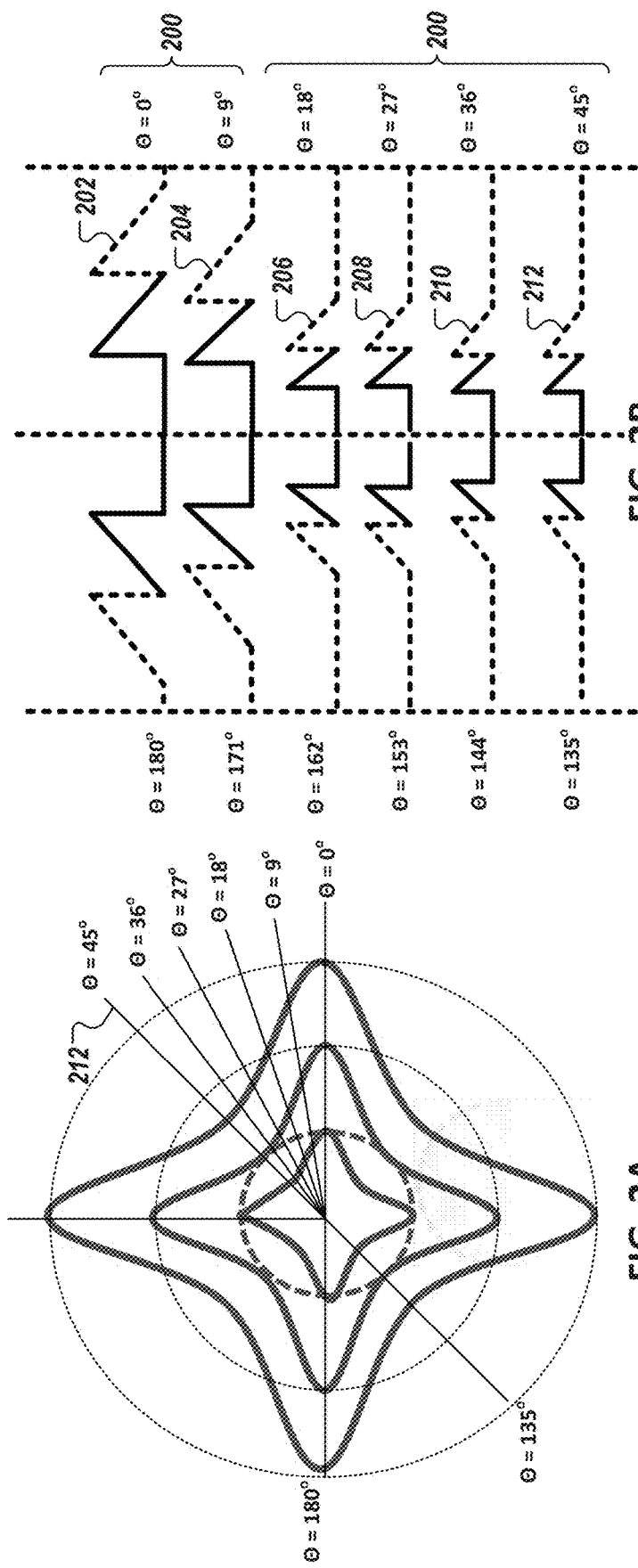
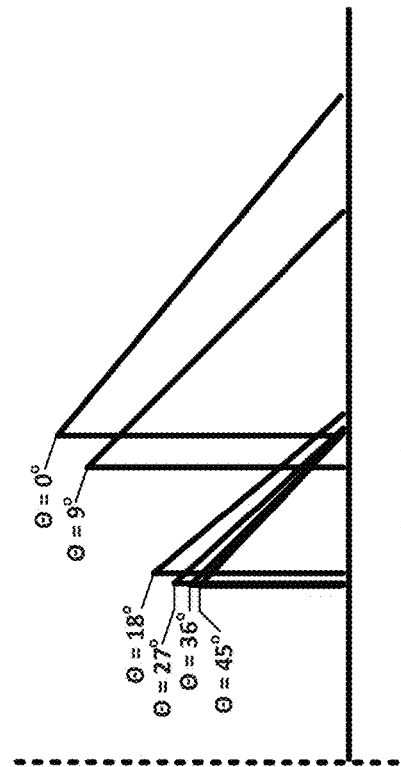
FIG. 2A
FIG. 2B
FIG. 2C

Tolerance of the misalignment of cylindrical axis

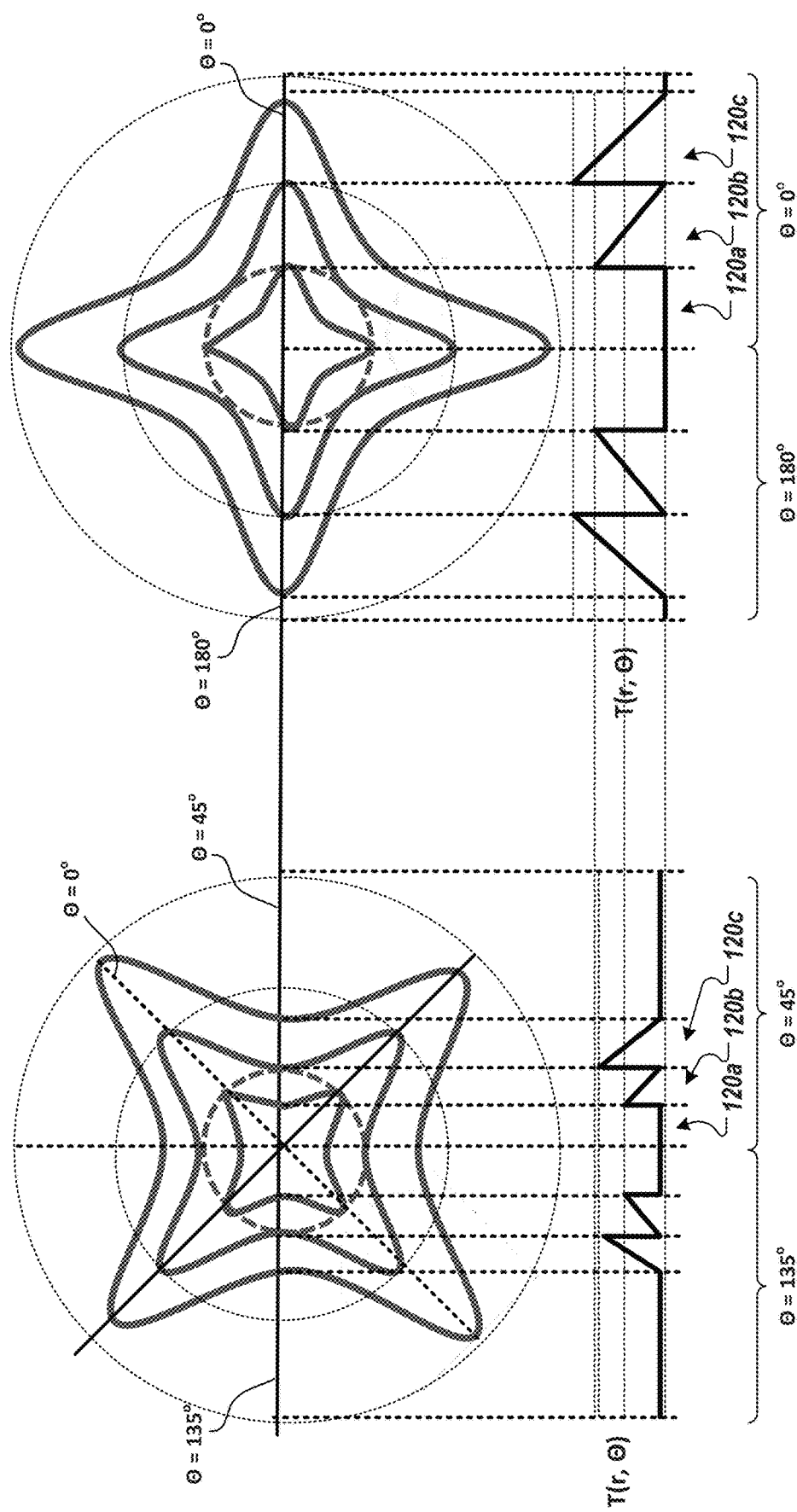

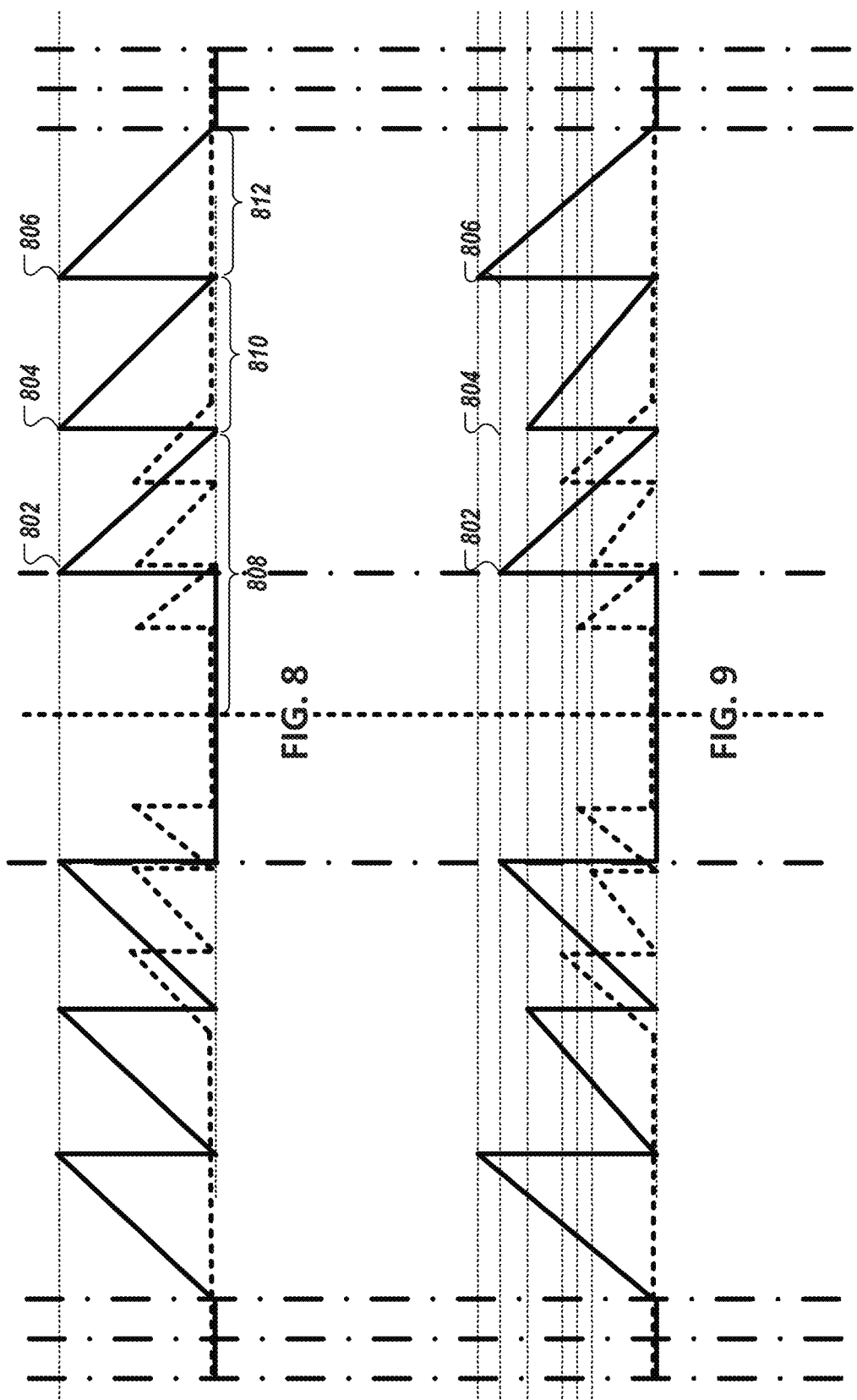

| Meridian | foci0 | Foci0 + add1 | foci0 − add2 | Chromatic aberration |
|---|---|---|---|---|
| 0 | 100 | 0 | 0 | reduced |
| ±45 | 50 | 25 | 25 | reduced |
| ±90 | 100 | 0 | 0 | reduced |
| ±135 | 50 | 25 | 25 | reduced |
| 180 | 100 | 0 | 0 | reduced |

Trifocal design example, in each foci Efficiency (%)

FIG. 14

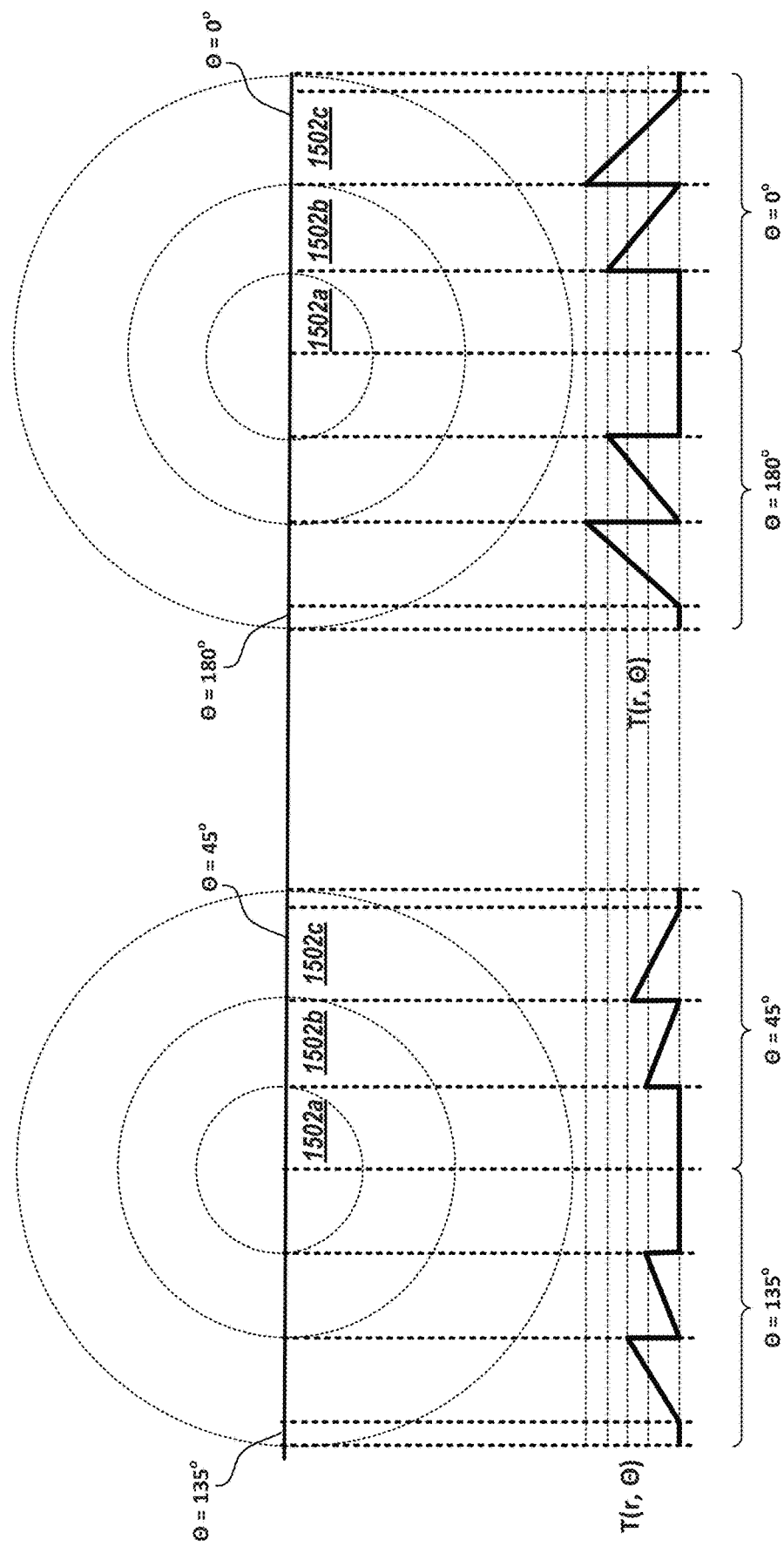

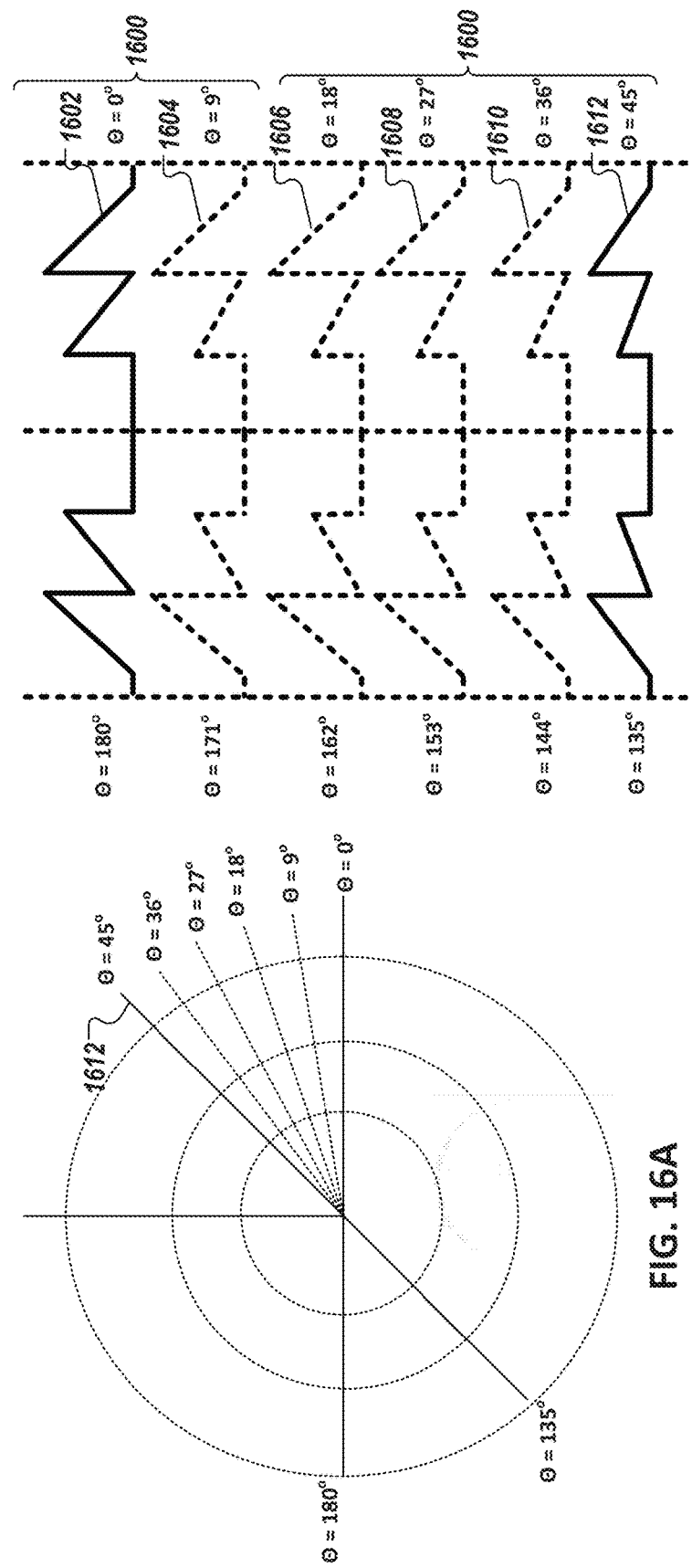
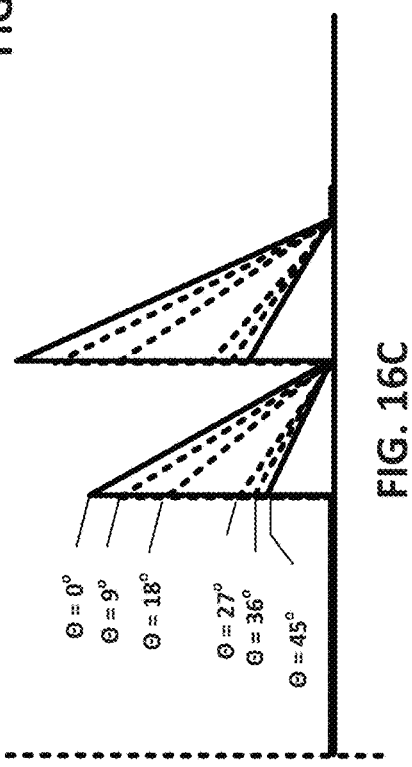
FIG. 16b
FIG. 16A
FIG. 16C

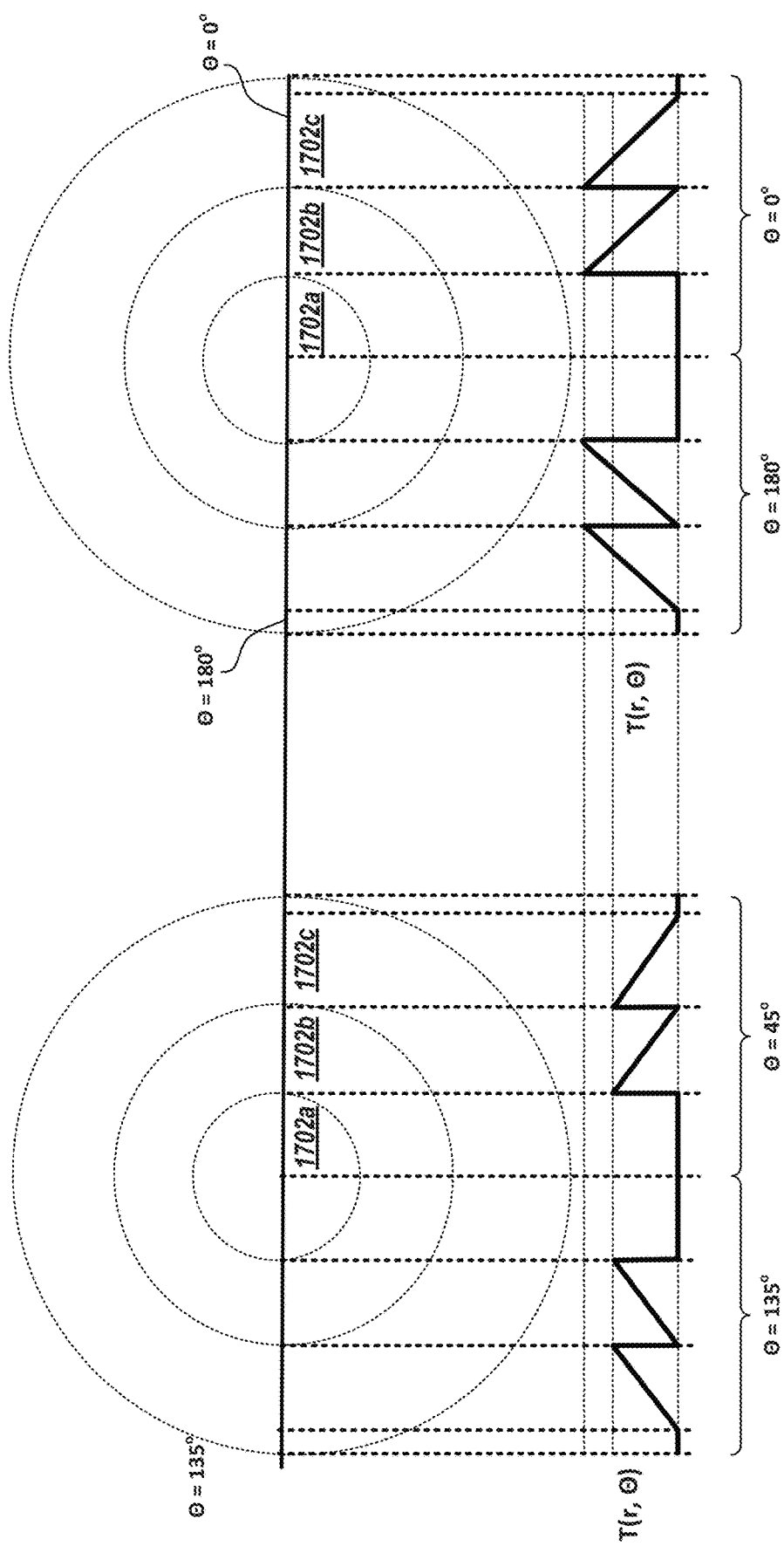

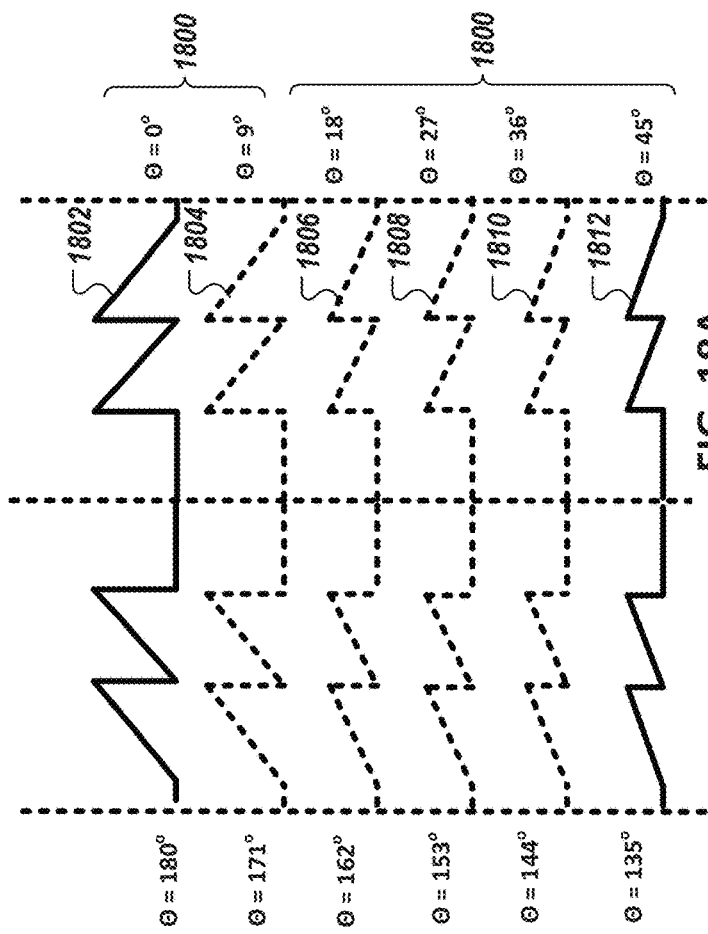
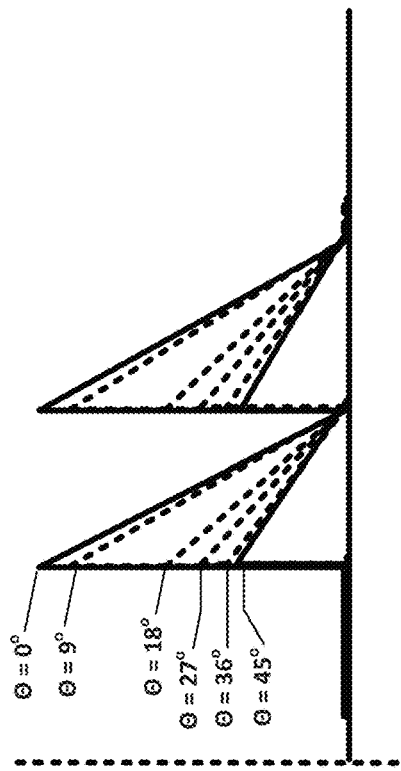
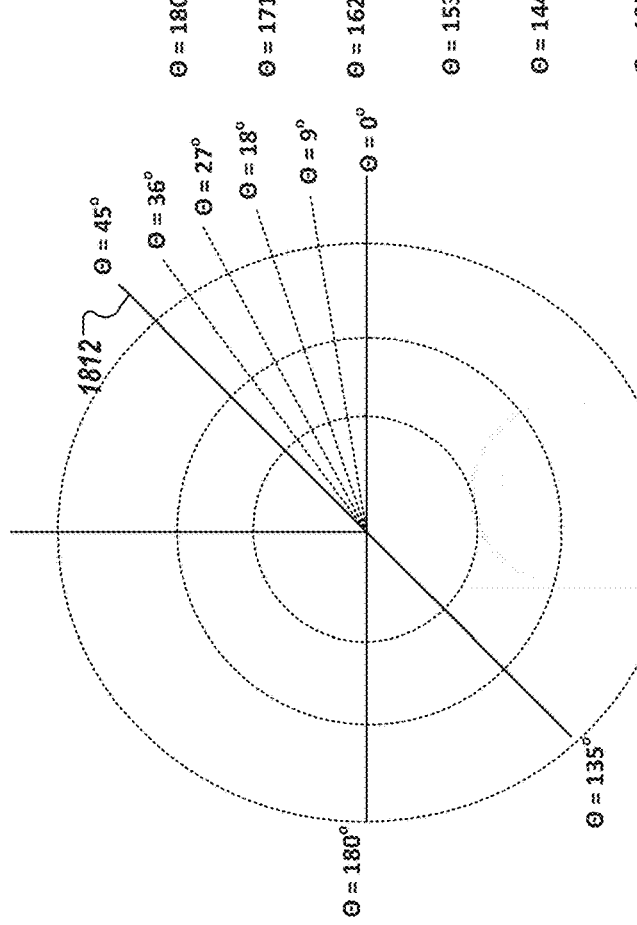
FIG. 18A
FIG. 18C
FIG. 18A

POWER CALCULATOR FOR AN OPHTHALMIC APPARATUS WITH CORRECTIVE MERIDIANS HAVING EXTENDED TOLERANCE OR OPERATION BAND

RELATED APPLICATIONS

This application claims priority to, and the benefit of, U.S. Provisional Appl. No. 62/312,321, filed Mar. 23, 2016; U.S. Provisional Appl. No. 62/312,338, filed Mar. 23, 2016; and 62/363,428, filed Jul. 18, 2016, each of which is incorporated by reference herein in its entirety.

TECHNICAL FIELD

This application is directed to providing correction for astigmatism, including provision to extend operable tolerance band of an ophthalmic apparatus to improve patient outcomes.

BACKGROUND

Ophthalmic lenses, such as spectacles, contact lenses and intraocular lenses, may be configured to provide both spherical and cylinder power. The cylinder power of a lens is used to correct the rotational asymmetric aberration of astigmatism of the cornea or eye, since astigmatism cannot be corrected by adjusting the spherical power of the lens alone. Lenses that are configured to correct astigmatism are commonly referred to as toric lenses. As used herein, a toric lens is characterized by a base spherical power (which may be positive, negative, or zero) and a cylinder power that is added to the base spherical power of the lens for correcting astigmatism of the eye.

Toric lenses typically have at least one surface that can be described by an asymmetric toric shape having two different curvature values in two orthogonal axes, wherein the toric lens is characterized by a "low power meridian" with a constant power equal to the base spherical power and an orthogonal "high power meridian" with a constant power equal to the base spherical power plus the cylinder power of the lens. Intraocular lenses, which are used to replace or supplement the natural lens of an eye, may also be configured to have a cylinder power for reducing or correcting astigmatism of the cornea or eye.

Existing toric lenses are designed to correct astigmatic effects caused by the corneal astigmatism by providing maximum cylindrical power that exactly matches the cylinder axis. Anchors are used to maintain the toric lenses at a desired orientations once implanted in the eye. However, existing toric lenses themselves are not designed to account for misalignments of the lens that may occur during the surgical implantation the lens in the eye or to account for unintended post-surgery movements of the lens in the eye.

Accordingly, it would be desirable to have interocular lenses that are tolerant to misalignments of lenses when implanted into the eye. In addition, it would be desirable to have a power calculator for such interocular lenses.

SUMMARY

The embodiments disclosed herein include improved toric lenses and other ophthalmic apparatuses (including, for example, contact lens, intraocular lenses (IOLs), and the like) (also referred to as a rotationally-extended tolerant IOL) and associated method for their design and use. In a preferred embodiment, an ophthalmic apparatus (e.g., a toric lens) includes one or more angularly-varying phase members, each varying depths of focus of the apparatus so as to provide an extended tolerance to misalignments of the apparatus when implanted in an eye. That is, the ophthalmic apparatus establishes a band of operational meridian over the intended correction meridian.

The ophthalmic apparatus includes a multi-zonal lens body having a plurality of optical zones, where the multi-zonal lens body forms the angularly-varying phase member. The angularly-varying phase member has a center at a first meridian (e.g., the intended correction meridian) that directs light to a first point of focus (e.g., at the retina of the eye). At angular positions nearby to the first meridian, the angularly-varying phase member directs light to points of focus of varying depths and nearby to the first point of focus such that rotational offsets of the multi-zonal lens body from the center of the first meridian directs light from the nearby points of focus to the first point of focus.

In some embodiments, the angularly-varying phase member includes a combination of angularly and zonally diffractive (or refractive) phase structure. This structure, in some embodiments, has a height profile (in relation to the face of the lens) that gradually varies along the angular position (i.e., at nearby meridian of the first meridian up) to provide off-axis operation up to a pre-defined angular position (e.g., about ±5° or more from the first meridian). In some embodiments, the height profile T1(r, θ) for the angularly-varying phase member at each meridian θ is defined as $T1(r, \theta) = t_1(r) \cdot |COS^2(\theta)| + t_2(r) \cdot |SIN^2(\theta)|$, where $t_1(r)$ and $t_2(r)$ are step heights that match an optical path difference (OPD) from 0 to 2λ, where λ, is the design wavelength at a zonal radius r. Put another way, each step heights $t_1(r)$ and $t_2(r)$ corresponds to a respective maximum and a minimum height (i.e., the peak and trough) of the angularly-varying phase member. In some embodiments, the angularly and zonally diffractive phase structure varies along each meridian between the first meridian (which has the step height $t_1(r)$) and meridian that are, in some embodiments, about 45 degrees and about −45 degrees to the first meridian.

In some embodiments, the angularly-varying phase member establishes the band of operational meridian across a range selected from the group consisting of about ±4 degrees, about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

In some embodiments, the multi-zonal lens body forms a second angularly-varying phase member at a second meridian that is orthogonal to the first meridian. The second angularly-varying phase member, in some embodiments, varies along each meridian nearby to the center of the second meridian i) between the second meridian and meridians that are, in some embodiments, about 45 degrees and about −45 degrees to the second meridian. In some embodiments, the first and second angularly-varying phase members form a butterfly pattern.

The first angularly-varying phase member and the second angularly-varying phase member, in some embodiments, form a double angularly varying efficiency bifocal optics.

In some embodiments, the multi-zonal lens body includes at least three optical zones that forms an angularly varying efficiency trifocal optics. In some embodiments, the multi-zonal lens body includes at least four optical zones that forms an angularly varying efficiency quadric optics.

In some embodiments, the angularly-varying phase member at the first meridian comprises a monofocal lens. In some embodiments, the second angularly-varying phase member at the second meridian comprises a second monofocal lens. In some embodiments, each of the meridians located at about 45 degrees and about −45 degrees to the first meridian comprises a bifocal lens.

In some embodiments, each of the angularly-varying phase structure of the multi-zonal lens body at the meridians located at about 45 degrees and about −45 degrees comprises a first optical zone, a second optical zone, and a third optical zone, wherein the first optical zone has a first point of focus and each of the second optical zone and the third optical zone has a respective point of focus nearby to the first point of focus, and wherein the first optical zone has a first light transmission efficiency (e.g., about 50%) and each of the second optical zone and the third optical zone has a respective light transmission efficiency (e.g., about 25% each) that is less than the first light transmission efficiency.

In some embodiments, the ophthalmic apparatus includes a plurality of alignment markings, including a first set of alignment markings and a second set of alignment markings. The first set of alignment markings corresponds to the center of the first meridian, and the second set of alignment markings corresponds to the band of operational meridian.

In another aspect, a rotationally-tolerant ophthalmic apparatus (e.g., toric interocular lens) having an established band of operation meridians (e.g., at least about ±4 degrees or more) for placement over an intended astigmatism meridian is disclosed. The ophthalmic apparatus includes a multi-zonal lens body having a plurality of optical zones, where the multi-zonal lens body forms the angularly-varying phase member. The angularly-varying phase member has a center at an astigmatism correction meridian that directs light to a first point of focus (e.g., on the retina). At angular positions nearby to the astigmatism correction meridian, the portion of the angularly-varying phase member at such angular positions directs light to points of focus of varying depths and nearby to the first point of focus such that rotational offsets of the multi-zonal lens body from the center of the astigmatism correction meridian directs light from the nearby points of focus to the first point of focus.

In another aspect, a rotationally-tolerant ophthalmic apparatus for correcting astigmatism is disclosed. The ophthalmic apparatus includes an astigmatism correcting meridian that corresponds to a peak cylinder power associated with a correction of an astigmatism. The rotationally-tolerant ophthalmic apparatus includes a plurality of exterior alignment markings, including a first set of alignment markings and a second set of alignment markings. The first set of alignment markings corresponds to the astigmatism correcting meridian, and the second set of alignment markings corresponds to an operation band of the rotationally-tolerant ophthalmic apparatus.

The embodiment disclosed herein further includes a system that performs a power calculator to determine the spherical equivalent (SE) and cylinder power for an extended tolerant toric lens and ophthalmic apparatuses having the extended band of operational meridian. In particular, this power calculator is selectable to account for the extended depth of focus, the extended depth of focus, the extended tolerance of astigmatism associated with the improved toric lens and ophthalmic apparatuses.

In some embodiments, the power calculator is configured to predict the SE and IOL for the extended tolerant IOL, including an IOL configured to provide an extended range of vision or ERV IOL including ERV toric IOL, an IOL configured to provide an extended depth of focus or EDOF IOL including toric EDOF IOL, and an IOL configured to provide an extended tolerance of astigmatism (effect) or ETA IOL.

In an aspect, a method is disclosed for determining optical configuration (e.g. IOL spherical equivalent and cylinder power) of a rotationally-extended tolerant ophthalmic apparatus for the selection thereof. The method includes receiving, by a processor, measurement data associated with an eye of a patient; determining, by the processor, using a conventional power calculator, a spherical equivalent and cylinder power using the measurement data for an ophthalmic apparatus selected from the group consisting of an implantable rotationally-extended tolerant ophthalmic apparatus, an implantable extended range of vision (ERV) ophthalmic apparatus, and an implantable extended depth of focus (EDOF) ophthalmic apparatus; determining, by the processor, a refractive or residual cylinder (RC) power associated with a random residual astigmatism power for the ophthalmic apparatus, wherein the random residual astigmatism power is associated with a pre-determined rotational misalignment for the apparatus once implanted; in response to a manifest refraction spherical equivalent (MRSE) parameter or manifest residential cylinder being outside an acceptable range of visual acuity, modifying the spherical equivalent by incrementally adding an incremental RC (e.g., ½ RC) thereto until the manifest refraction spherical equivalent (MRSE) parameter or manifest residential cylinder is within the acceptable range; and causing, by the processor, a visual representation of the spherical equivalent and cylinder power to be presented, wherein the spherical equivalent and cylinder power are used for the selection of the implantable ophthalmic apparatus to be implanted into the eye of the patient.

In some embodiments, the incremental RC is about 0.1 RC, about 0.2 RC, about 0.3 RC, about 0.4 RC, about 0.5 RC, about 0.6 RC, about 0.7 RC, about 0.8 RC, about 0.9 RC.

In some embodiments, the implantable ophthalmic apparatus comprises the implantable rotationally-extended tolerant ophthalmic apparatus.

In some embodiments, the implantable ophthalmic apparatus comprises the implantable extended range of vision (ERV) ophthalmic apparatus.

In some embodiments, implantable ophthalmic apparatus comprises the implantable extended depth of focus (EDOF) ophthalmic apparatus.

In some embodiments, the pre-determined rotational misalignment is a maximum expected rotational misalignment value determined for the given implantable ophthalmic apparatus.

In some embodiments, the maximum expected rotational misalignment value is a maximum misaligned angle from an intended meridian, selected from the group consisting of ±2°, ±3°, ±4°, ±5°, ±6°, ±7°, ±8°, ±9°, and ±10°.

In some embodiments, the method further includes modifying the spherical equivalent by a value corresponding to the residual refractive error, wherein the residual refractive error is expressed in spherical equivalent.

In some embodiments, the acceptable range of visual acuity comprises an uncorrected visual acuity (UCVA) state.

In some embodiments, the refractive or residual cylinder (RC) power associated with the random residual astigmatism power for the ophthalmic apparatus is calculated as $OC = 2 \sin \alpha * C/2 \; 0.7 \cos(2(\theta+90+\alpha/2))$, wherein $\theta$ is an intended correction meridian expressed in degrees; C is the astigmatic power, at the IOL plane, to be corrected at meridian $\theta$, expressed in Diopters; and $\alpha$ is the magnitude of rotational misalignment of the cylindrical power axis to the astigmatic axis, expressed in degrees.

In some embodiments, the method further includes determining, by the processor, a potential manifest refraction spherical equivalent parameter and manifest residual cylinder tolerance level.

In another aspect, a non-transitory computer readable medium, the computer readable medium having instructions stored thereon, wherein the instructions, when executed by a processor, cause the processor to: receive measurement data associated with an eye of a patient; determine using a conventional power calculator, a spherical equivalent and cylinder power using the measurement data for an ophthalmic apparatus selected from the group consisting of an implantable rotationally-extended tolerant ophthalmic apparatus, an implantable extended range of vision (ERV) ophthalmic apparatus, and an implantable extended depth of focus (EDOF) ophthalmic apparatus; determine a refractive or residual cylinder (RC) power associated with a random residual astigmatism power for the ophthalmic apparatus, wherein the random residual astigmatism power is associated with a pre-determined rotational misalignment for the apparatus once implanted; in response to a manifest refraction spherical equivalent (MRSE) parameter or manifest residential cylinder being outside an acceptable range of visual acuity, modify the spherical equivalent by incrementally adding increment RC (e.g., ½ RC) thereto until the manifest refraction spherical equivalent (MRSE) parameter or manifest residential cylinder is within the acceptable range; and cause a visual representation of the spherical equivalent and cylinder power to be presented, wherein the spherical equivalent and cylinder power are used for the selection of the implantable ophthalmic apparatus to be implanted into the eye of the patient.

In some embodiments, the implantable ophthalmic apparatus comprises the implantable rotationally-extended tolerant ophthalmic apparatus.

In some embodiments, the implantable ophthalmic apparatus comprises the implantable extended range of vision (ERV) ophthalmic apparatus.

In some embodiments, the implantable ophthalmic apparatus comprises the implantable extended depth of focus (EDOF) ophthalmic apparatus.

In some embodiments, the pre-determined rotational misalignment is a maximum expected rotational misalignment value determined for the given implantable ophthalmic apparatus.

In some embodiments, the maximum expected rotational misalignment value is a maximum misaligned angle from an intended meridian, selected from the group consisting of $\pm 2°$, $\pm 3°$, $\pm 4°$, $\pm 5°$, $\pm 6°$, $\pm 7°$, $\pm 8°$, $\pm 9°$, and $\pm 10°$.

In some embodiments, the instructions, when executed by the processor, cause the processor to: modify the spherical equivalent by a value corresponding to the residual refractive error, wherein the residual refractive error is expressed in spherical equivalent.

In some embodiments, the acceptable range of visual acuity comprises an uncorrected visual acuity (UCVA) state.

In some embodiments, the refractive or residual cylinder (RC) power associated with the random residual astigmatism power for the ophthalmic apparatus is calculated as: $OC = 2 \sin \alpha * C/2 \ 0.7 \cos(2(\theta + 90 + a/2))$, wherein $\theta$ is an intended correction meridian expressed in degrees; C is the astigmatic power, at the IOL plane, to be corrected at meridian $\theta$, expressed in Diopters; and a is the magnitude of rotational misalignment of the cylindrical power axis to the astigmatic axis, expressed in degrees.

In some embodiments, the instructions, when executed by the processor, cause the processor to: determine a potential manifest refraction spherical equivalent parameter and manifest residual cylinder tolerance level.

In some embodiments, the incremental RC is about 0.1 RC, about 0.2 RC, about 0.3 RC, about 0.4 RC, about 0.5 RC, about 0.6 RC, about 0.7 RC, about 0.8 RC, about 0.9 RC.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIGS. 2A, 2B, and 2C illustrate a plurality of exemplary height profiles of the anterior or posterior face of the ophthalmic apparatus of FIGS. 1A-1B in accordance with an illustrative embodiment.

FIGS. 7A and 7B are diagrams of an exemplary ophthalmic apparatus that includes angularly-varying phase members in accordance with another illustrative embodiment.

FIGS. 8 and 9 are diagrams illustrating height profiles of exemplary ophthalmic apparatuses of FIGS. 1 and 7 in accordance with the illustrative embodiments.

FIG. 14 is a table of the ophthalmic apparatus of FIG. 13 configured as a tri-focal lens in accordance with an illustrative embodiment.

FIGS. 15A and 15B are diagrams of an exemplary ophthalmic apparatus that includes angularly-varying phase members and an asymmetric height profile in accordance with an illustrative embodiment.

FIGS. 16A, 16B and 16C illustrate a plurality of exemplary height profiles of the ophthalmic apparatus of FIG. 15 in accordance with an illustrative embodiment.

FIGS. 17A and 17B are diagrams of an exemplary ophthalmic apparatus that includes angularly-varying phase members and a symmetric height profile in accordance with another illustrative embodiment.

FIGS. 18A, 18B and 18C illustrate a plurality of exemplary height profiles of the anterior or posterior face of the ophthalmic apparatus of FIG. 17 in accordance with an illustrative embodiment.

DETAILED DESCRIPTION OF THE PREFERRED EMBODIMENT

Each and every feature described herein, and each and every combination of two or more of such features, is included within the scope of the present invention provided that the features included in such a combination are not mutually inconsistent.

Embodiments of the present invention are generally directed to toric lenses or surface shapes, and/or related methods and systems for fabrication and use thereof. Toric lenses according to embodiments of the present disclosure find particular use in or on the eyes of human or animal subjects. Embodiments of the present disclosure are illustrated below with particular reference to intraocular lenses; however, other types of lenses fall within the scope of the present disclosure. Embodiments of the present disclosure provide improved ophthalmic lens (including, for example, contact lenses, and interocular lenses, corneal lenses and the like) and include monofocal diffractive lenses, bifocal diffractive lenses, and multifocal diffractive lenses.

As used herein, the term "optical power" means the ability of a lens or optics, or portion thereof, to converge or diverge light to provide a focus (real or virtual), and is commonly specified in units of reciprocal meters ($m^{-1}$) or Diopters (D). When used in reference to an intraocular lens, the term "optical power" means the optical power of the intraocular lens when disposed within a media having a refractive index of 1.336 (generally considered to be the refractive index of the aqueous and vitreous humors of the human eye), unless otherwise specified. Except where noted otherwise, the optical power of a lens or optic is from a reference plane associated with the lens or optic (e.g., a principal plane of an optic). As used herein, a cylinder power refers to the power required to correct for astigmatism resulting from imperfections of the cornea and/or surgically induced astigmatism.

As used herein, the terms "about" or "approximately", when used in reference to a Diopter value of an optical power, mean within plus or minus 0.25 Diopter of the referenced optical power(s). As used herein, the terms "about" or "approximately", when used in reference to a percentage (%), mean within plus or minus one percent (±1%). As used herein, the terms "about" or "approximately", when used in reference to a linear dimension (e.g., length, width, thickness, distance, etc.) mean within plus or minus one percent (1%) of the value of the referenced linear dimension.

Figures 1A, 1B:
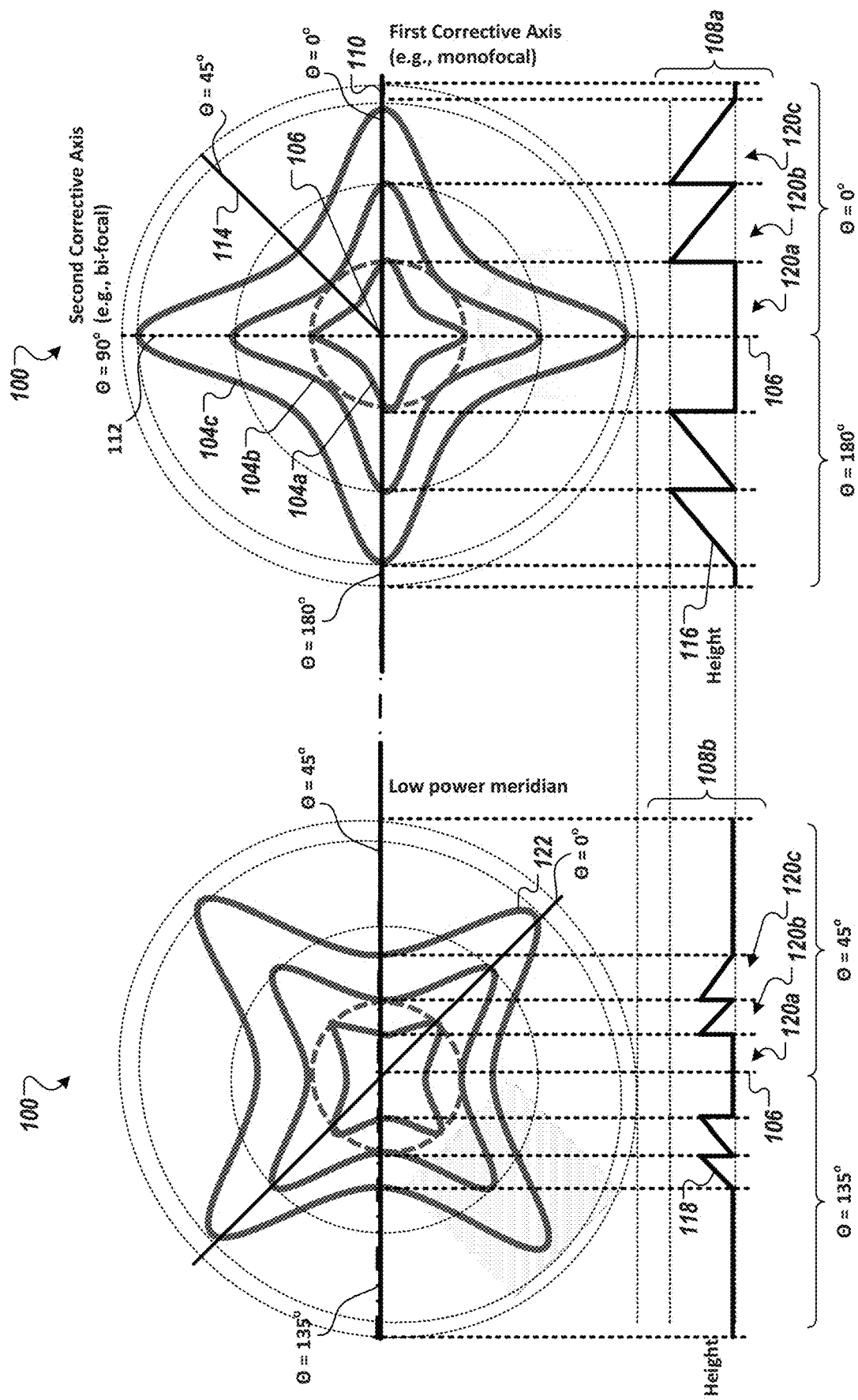
FIGS. 1A and 1B are diagrams of an exemplary ophthalmic apparatus (e.g., an interocular toric lens) that includes angularly-varying phase members (reflective, diffractive, or both) that provide an extended rotational tolerance of the apparatus in accordance with an illustrative embodiment.

FIGS. 1A and 1B are diagrams of an exemplary ophthalmic apparatus 100 (e.g., an interocular toric lens) that includes angularly-varying phase members (reflective, diffractive, or both) configured to provided extended rotational tolerance in accordance with an illustrative embodiment.

The angularly-varying phase members has a center structure that applies cylinder power at a corrective meridian (e.g., the high power meridian). Off-center structures of the angularly-varying phase members extends from the center structure in a gradually varying manner to apply cylinder power to a band of meridians surrounding the corrective meridian enabling the ophthalmic apparatus to operate off-axis (or off-meridian) to the corrective meridian (e.g., the astigmatism meridian). These meridians may be referred to as a dynamic meridian.

The angularly-varying phase members, in some embodiments, includes an optimized combination of angularly and zonally diffractive (or refractive) phase structure located at each meridian to vary the extended depth of focus to a plurality of nearby focus points. Light directed to such nearby focus points are thus directed to the desired focus point when the ophthalmic apparatus is subjected to a rotational offset from a primary intended axis of alignment, thereby extending the rotational tolerance of the apparatus to an extended tolerance band. This may also be referred to as "extended tolerance astigmatism band" or "extended misalignment band." Remarkably, this extended tolerance astigmatism band delivers cylinder power to correct for the astigmatism for a range of meridians (e.g., up to ±5° or more), thereby eliminating any need for additional corrective measures (e.g., supplemental corrective devices or another surgical interference) when the implanted ophthalmic apparatus is not perfectly aligned to the desired astigmatism meridian in the eye.

Put another way, the angularly-varying phase members enable an extended band of the corrective meridian (e.g., up to 10° or more) that has minimal, and/or clinically acceptable, degradation of the visual acuity and modulation transfer function when the ophthalmic apparatus is subject to rotational misalignment between the astigmatic axis and a center axis of the corrective meridian.

In some embodiments, an exemplified toric intraocular lens (IOL) includes dynamic meridian or angularly varying efficiency quadric optics. In another embodiments, an exemplified toric IOL includes dynamic meridian or angularly varying efficiency trifocal optics. In another embodiments, an exemplified toric IOL includes double dynamic meridian or angularly varying efficiency bifocal optics. In another embodiments, the bifocal or trifocal feature may be disposed on one optical surface or on both optical surfaces of a single optical lens or on any surfaces of a multiple optical elements working together as a system.

Referring still to FIGS. 1A and 1B, an embodiment of the angularly-varying phase members is shown. In this embodiment, the angularly-varying phase members is formed in a multiple-zone structure (shown as zones 120a, 120b, 120c), each having a spatially-varying "butterfly" shaped structure centered around the optical axis 106. The multiple-zone structure and angularly-varying phase members therein form a first "high power meridian" (e.g., having a constant power equal to the base spherical power plus a cylinder power of the lens) at a first meridian (e.g., axis 110 shown as θ=0°) that corresponds to an axis of the eye to apply a correction. The first corrective meridian 110 focuses light that passes therethrough to a first foci (i.e., point of focus) and is intended to align with the astigmatic axis of the eye. At nearby meridians, the angularly-varying phase members focus light that passes therethrough to a plurality of foci near the first foci. The angularly-varying phase members varies from between the first meridian (θ=0°) and another meridian located about 45 degrees from the first meridian (e.g., axis 114 shown as θ=45°).

As shown in FIGS. 1A and 1B, both the heights of the lens and the spatial sizes, at each zone varies among the different axes to form the angularly-varying phase member. To illustrate this structure, both a first height profile 116 of the lens along the first corrective meridian (θ=0°) and a second height profile 118 of the lens along a lower power meridian (i.e., axis 114 shown as θ=45°) are presented at plots 108a and 108b, respectively, for each of FIGS. 1A and 1B. The height profile of the lens varies at each axis as the first height profile gradually transitions (e.g., as shown by the curved profile 122) into the second height profile. The first and second height profiles 116 and 118 are illustrated relative to one another in a simplified format. It should be appreciated that the height profiles are superimposed on a lens having a curvature, as for example, illustrated in FIG. 3.

It should be appreciated that the height profiles herein are illustrated in a simplified form (e.g., as a straight line). The height profiles for each zone may have other shapes—such as convex, concave, or combinations thereof.

Referring still to FIGS. 1A and 1B, the multiple-zone structure and angularly-varying phase members therein form a second "high power meridian" 112 (i.e., axis 112 shown as θ=90°) which is orthogonal to the first corrective meridian 110. The second corrective meridian 112 focuses light to a second set of foci.

FIGS. 2A, 2B, and 2C illustrate a plurality of height profiles of the angularly-varying phase member of FIGS. 1A-1B between the first high power meridian (at θ=0°) and a low power meridian (at θ=45°) in accordance with an illustrative embodiment. In FIG. 2B, height profiles at θ=0° (202); θ=9° (204); θ=18° (206); θ=27° (208); θ=36° (210); and θ=45° (212) (also shown in FIG. 2A) are provided as cross-sections of the apparatus at different meridians shown in FIG. 2A. As shown, the height profiles at axes nearby to the first high power meridian (e.g., between ±5°) have a similar height profile, as the first high power meridian. The height profile varies in a continuous gradual manner (e.g., having a sine and cosine relationship) along the radial direction. This can be observed in FIGS. 2B and 2C. In FIG. 2B, the height profile of the lens at θ=9° (204) is similar in magnitude and phase in relation to the height profile of the lens at θ=0° (202). The height profile of the lens is shown to transition more abruptly at θ=18° (206); θ=27° (208); θ=36° (210); and θ=45° (212), which are similar in magnitude and phase to one another. FIG. 2C illustrates a first portion of the height profiles (near the optical axis) at θ=0° (202); θ=9° (204); θ=18° (206); θ=27° (208); θ=36° (210); and θ=45° (212) superimposed to one another. This variation of the height profile along the radial axis provides a lens region that focuses light at the desired foci and other foci nearby. To this end, radial offset (i.e., misalignment) of the ophthalmic apparatus from the center axis of a desired corrective meridian results in its nearby regions focusing the light to the desired foci. This effect is further illustrated in FIG. 3.

Figure 3:
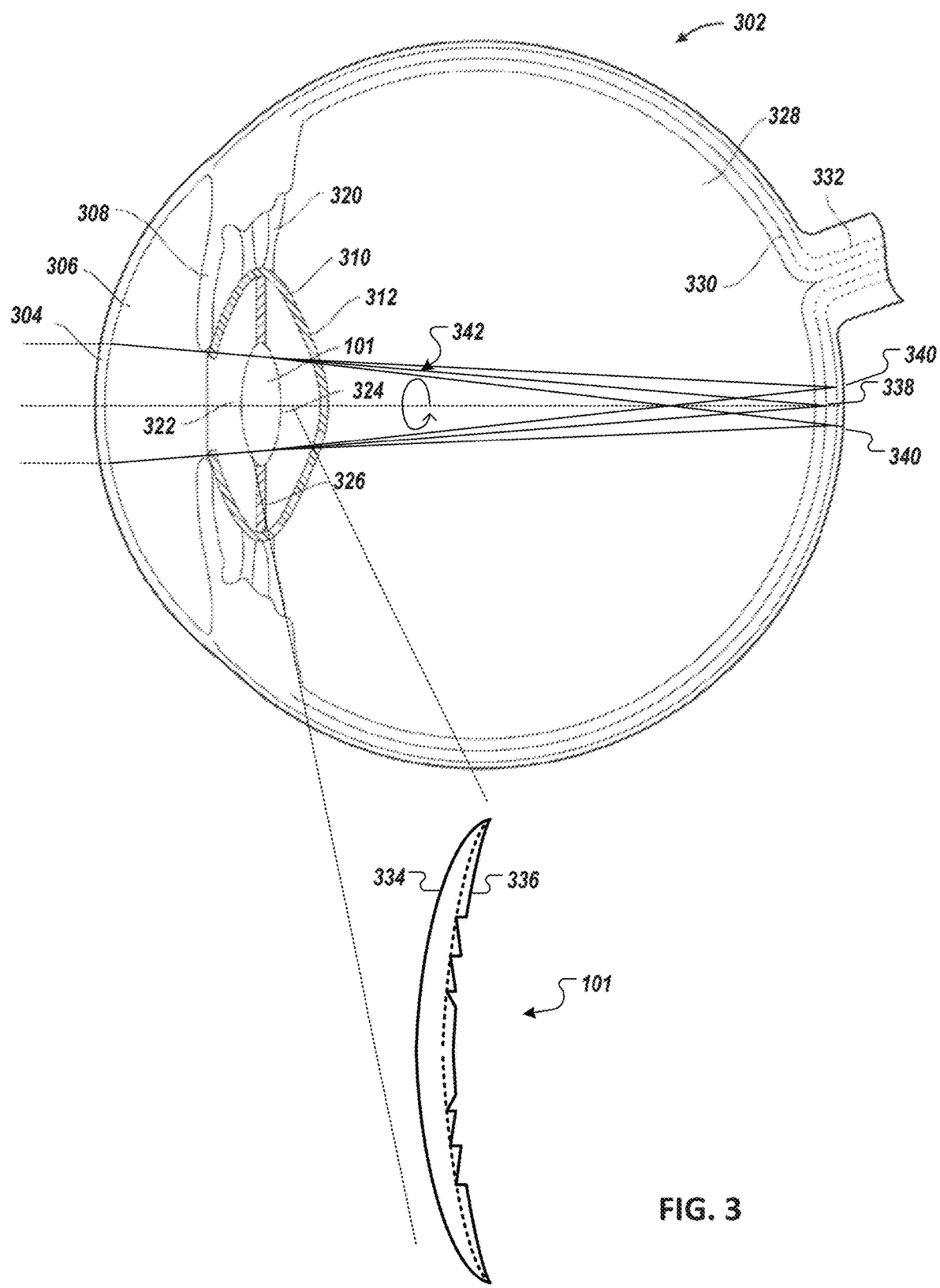
FIG. 3 is a schematic drawing of a top view of a human eye, in which the natural lens of the eye has been removed and replaced with an ophthalmic apparatus that includes angularly-varying phase members in accordance with an illustrative embodiment.

FIG. 3 is a schematic drawing of a top view of a human eye 302, in which the natural lens of the eye has been removed and replaced with an intraocular lens 100 (shown in simplified form in the upper portion of FIG. 3 and in greater detail in the lower portion of FIG. 3). Light enters from the left of FIG. 3, and passes through the cornea 304, the anterior chamber 306, the iris 308, and enters the capsular bag 310. Prior to surgery, the natural lens occupies essentially the entire interior of the capsular bag 310. After surgery, the capsular bag 310 houses the intraocular lens 100, in addition to a fluid that occupies the remaining volume and equalizes the pressure in the eye.

After passing through the intraocular lens, light exits the posterior wall of the capsular bag 310, passes through the posterior chamber 328, and strikes the retina 330, which detects the light and converts it to a signal transmitted through the optic nerve 332 to the brain. The intraocular lens comprises an optic 101 and may include one or more haptics 326 that are attached to the optic 101 and may serve to center the optic 101 in the eye and/or couple the optic 101 to the capsular bag 310 and/or zonular fibers 320 of the eye.

The optic 101 has an anterior surface 334 and a posterior surface 336, each having a particular shape that contributes to the refractive properties of the lens. Either or both of these lens surfaces may optionally have an element made integral with or attached to the surfaces. The refractive and/or diffractive elements on the anterior and/or posterior surfaces, in some embodiments, have anamorphic or toric features that can generate astigmatism to offset the astigmatism from a particular cornea in an eye. The optics 101, in some embodiments, comprises the interocular lens 100.

Referring still to FIG. 3, the interocular lens 101 includes angularly-varying phase members (reflective, diffractive, or both) that focus at a plurality of focus points that are offset radially to one another so as to provide an extended tolerance to misalignments of the lens 100 when implanted into the eye 302. That is, when the center axis of a corrective meridian is exactly matched to the desired astigmatic axis, only a first portion of the cylinder axis is focused at the desired point of focus (338) (e.g., at the retina) while second portions of the cylinder axis focuses at other points (340) nearby that are radially offset to the desired point of focus (338). To this end, when the primary axis of the astigmatism of the interocular lens is rotationally offset (shown as arrow 342) with the astigmatism of the eye, the second portion of the cylinder axis focuses the light to the desired point of focus.

Artificial lenses (e.g., contact lenses or artificial intraocular lenses) can correct for certain visual impairments such as an inability of the natural lens to focus at near, intermediate or far distances; and/or astigmatism. Intraocular toric lenses have the potential for correcting astigmatism while also correcting for other vision impairments such as cataract, presbyopia, etc. However, in some patients implanted intraocular toric lenses may not adequately correct astigmatism due to rotational misalignment of the corrective meridian of the lenses with the astigmatic meridian. In some patients following the surgical implant of the toric lenses, the corrective meridian of the implanted toric lenses can be rotationally misaligned to the astigmatic meridian, in some instances, by as much as 10 degrees. However, toric lenses that are designed to provide maximum correction (e.g., 1 D to 9 D) at the astigmatic meridian are subject to significant reduction in effectiveness of the correction due to any misalignment from the corrective meridian. In certain designs, it is observed that if the cylindrical power axis were mismatched by 1 degree, there would be about 3 percent reduction of the effectiveness of the correction. The degradation increases with the degree of misalignment. If there were a 10-degree misalignment, there would be about 35% reduction of the effectiveness of the correction. This effect is illustrated in FIG. 4 discussed below.

Figure 4A:
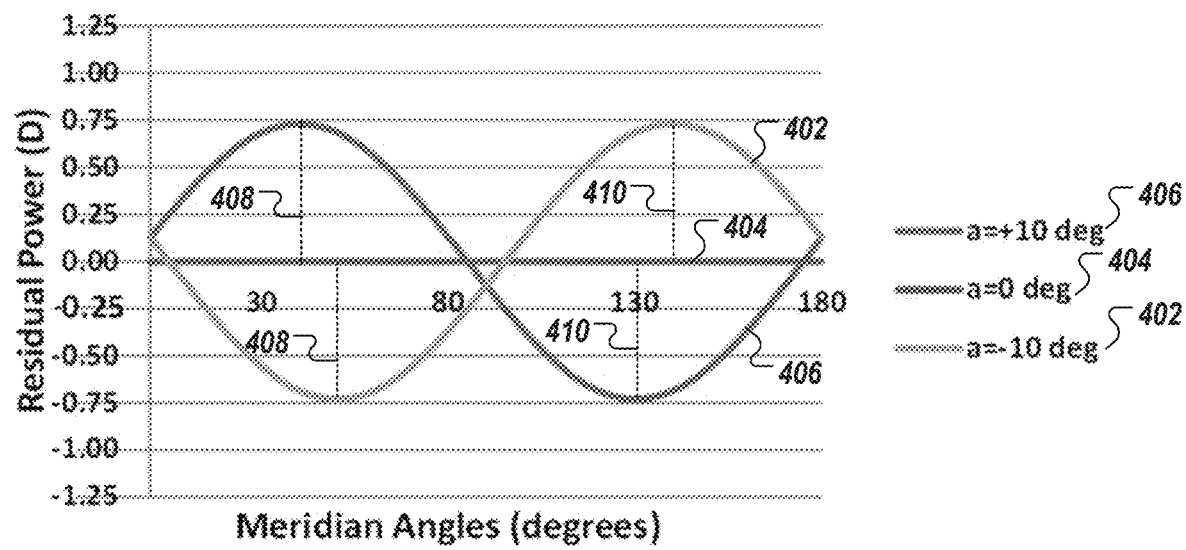
FIGS. 4A and 4B are plots illustrating performance of a conventional toric lens designed to apply maximum cylinder power at a corrective meridian when subjected to rotational misalignment.
Figure 4B:
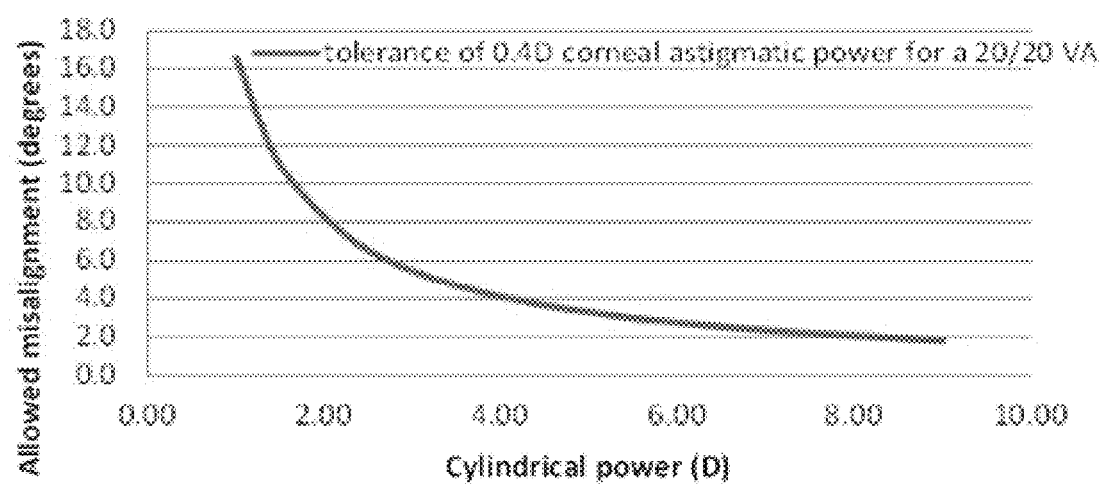

FIG. 4, comprising FIGS. 4A and 4B, includes plots that illustrated the above-discussed degraded performance of conventional toric lens when subjected to rotational misalignment. This conventional toric lens is configured to provide 6.00 Diopters cylinder powers at the IOL plane, 4.11 Diopters cylinder power at the corneal plane, and a corneal astigmatism correction range (i.e., preoperative corneal astigmatism to predicted effects) between 4.00 and 4.75 Diopters.

Referring to FIG. 4A, a plot of undesired meridian power (also referred to as a residual meridian power ("OC")) (shown along the y-axis) added due to the rotational misalignments (shown along the x-axis) of the toric IOL is shown, including the residual powers for a negative 10-degree misalignment (shown as line 402), a 0-degree misalignment (shown as line 404), and a positive 10-degree misalignment (shown as line 406). As shown, the undesired added meridian power varies between a maximum of ±0.75 Diopters at around the 45-degree meridian angle (shown as 408) and at about the 135-degree meridian angle (shown as 410). Notably, this undesired added meridian power is outside the tolerance of a healthy human eye, which can tolerant undesired effects up to about 0.4 Diopters (e.g., at the cornea plane) for normal visual acuity (i.e., "20/20 vision"). Because the undesired effects exceeds the astigmatism tolerance of the human eye, corrective prescription glasses, or further surgical operation to correct the implant misalignment, may be necessary to mitigate the effects of the misalignment of such toric IOLs.

This undesired meridian power may be expressed as Equation 1 below.

$$OC = 2\sin\alpha * \frac{C}{2}0.7\cos\left(2\left(\theta + 90 + \frac{\alpha}{2}\right)\right) \quad \text{(Equation 1)}$$

As shown in Equation 1, θ is the correction meridian (also referred to as the cylindrical power axis) (in degrees); C is the astigmatic power (at the IOL plane) to be corrected at meridian θ (in Diopters); and a is the magnitude of rotational misalignment of the cylindrical power axis to the astigmatic axis (in degrees).

FIG. 4B shows a plot illustrating the tolerance of a toric IOL to misalignment (shown in the y-axis) and a corresponding cylindrical power that may be applied (shown in the x-axis) for each misalignment to not exceed the astigmatism tolerance of the human eye (i.e., degrade the overall visual acuity). The tolerance to misalignment may be calculated as $$|\alpha| \le \sin^{-1}\frac{\frac{0.4}{2}}{\frac{C}{0.7}}$$

where α is the magnitude of rotational misalignment (in degrees). The calculation may be reduced to $$|\alpha| \le \sin^{-1}\frac{0.29}{C}.$$

As shown, for a misalignment of 5 degrees, which is routinely observed in IOL implantations, the correction effectiveness of such IOL implants can only be maintained for a toric IOL with 3.75 Diopters or less. That is, a toric IOL having cylinder power above 3.75 Diopters would exhibit degraded visual acuity due to the residual power exceeding the astigmatism tolerance of a human eye. This effect is worsen with further degrees of misalignment. For example, at about 10 degrees, the effectiveness of a toric IOL is greatly reduced where only 1.5 Diopters cylinder power or less can be applied so as to not detrimentally effect the visual acuity. Given that cylinder power of convention toric IOLs may range between 1.00 Diopters and 9.00 Diopters, these toric IOLs are reduced in effectiveness post-operation due to the misalignments of cylinder axis.

Figure 5:
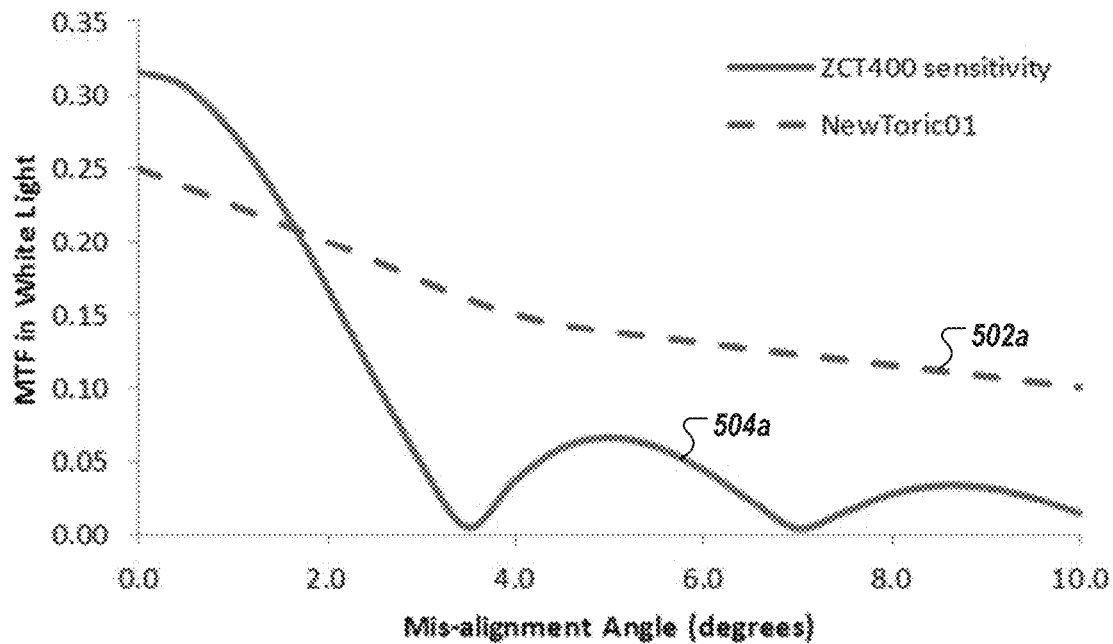
FIGS. 5 and 6 show plots of off-axis performances of an exemplary ophthalmic apparatus (diffractive and refractive) that includes angularly-varying phase members in accordance with an illustrative embodiment.
Figure 6:
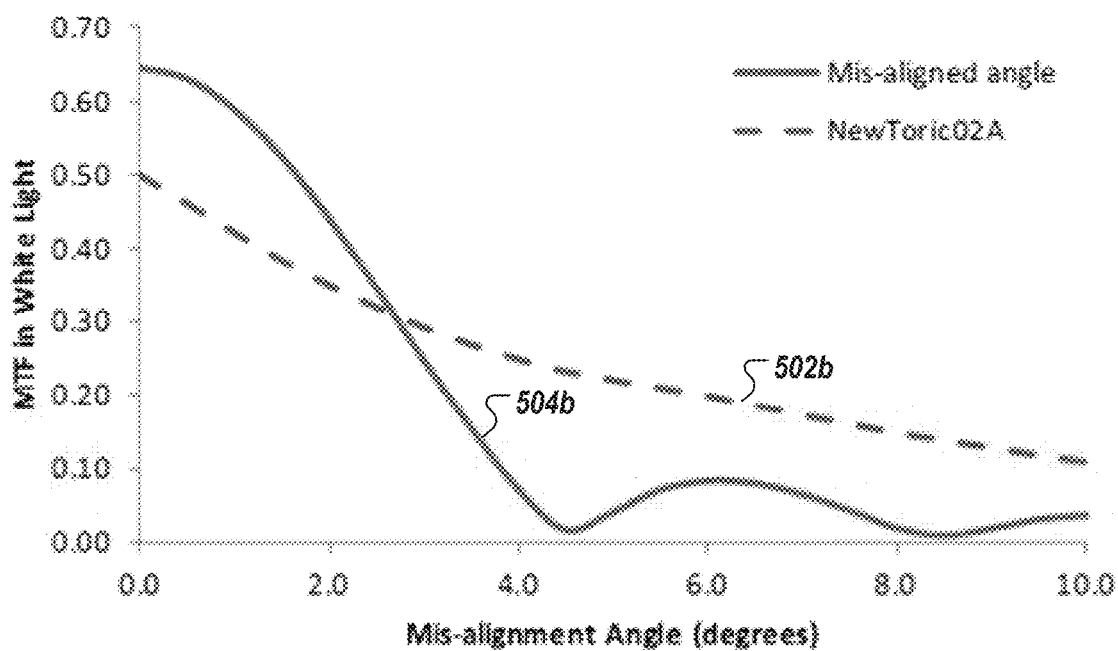

Each of FIGS. 5 and 6 shows plots illustrating modular transfer functions (MTFs) in white light for two toric IOLs (shown as 502a and 502b) each configured with angularly-varying phase members when subjected to off-axis rotations. FIG. 5 illustrates the performance for a refractive toric IOL, and FIG. 6 illustrates performance for a diffractive toric IOL.

Remarkably, the cylinder power of the lens configured with angularly varying phase member provides an extended tolerance of misalignment up to 10 degrees and more of off-axis rotation. As shown, the modulation transfer function (MTF) is maintained across the extended range of alignment for a lens configured with the angularly varying phase member. In contrast, at certain degrees of misalignment, the MTF of a toric IOL without the angularly varying phase member is near zero. For example, as shown, the MTF at 3.5 degrees misalignment for a conventional toric lens is near zero. MTF is a modulation of the amplitude and phase functions of an image formed by the white light on a specified plane, for example, the retina of the human eye, and characterizes the sensitivity of the lens.

Referring still to FIGS. 5 and 6, an ophthalmic apparatus that includes angularly varying phase members has a lower maximum cylinder range (as compared to lens without such structure). Rather, the angularly varying phase members applies the cylinder power to a band surrounding the corrective meridian, thereby providing a continuous band that makes the lens may tolerant due to misalignment. As shown, in this embodiment, the sensitivity of the ophthalmic apparatus with the angularly varying phase member is less by 20% as compared to a lens without the angularly varying phase member. And, at 10 degrees of misalignment (or off-axis operation) from the targeted corrective axis, the modulation transfer function (MTF) degradation for the ophthalmic apparatus configured with the angularly varying phase member is still acceptable. In this example, the ophthalmic apparatus configured with the angularly varying phase member is configured as a monofocal toric lens with 4.0 Diopters cylindrical power. Here, the MTF is at 100 lp/-mm and has a spatial frequency equivalent to 30 c/degree for an emmetropia eye with 20/20 visual acuity. The performance of the toric IOL with the angularly varying phase member at 5 degrees off-meridian has comparable MTF performance to a similar toric IOL without the structure at 2 degrees of misalignment.

FIG. 7 is a diagram of an ophthalmic apparatus 100 (e.g., an interocular toric lens) that includes angularly-varying phase members (reflective, diffractive, or both) that disperse light therethrough to a plurality of foci that are offset radially to one another so as to provide an extended tolerance to misalignments of the lens 100 when implanted in an eye in accordance with another illustrative embodiment. As shown in FIG. 7, the apparatus 100 has an asymmetric height profile 702 in which the maximum height of the face 704 of the apparatus differs between the different zones (see zones 120b and 120c).

In some embodiments, the asymmetric height profile may be configured to direct light to a plurality foci. For example, the apparatus 100 with the asymmetric height profile 702 may be used for as a trifocal lens. In other embodiments, the apparatus with the asymmetric height profile 702 is used for a quad-focal lens. In some embodiments, the apparatus 100 with the asymmetric height profile 702 is used for a double bi-focal lens. In some embodiments, the apparatus 100 with the asymmetric height profile 702 is used for a mono-focal lens. In some embodiments, the apparatus 100 with the asymmetric height profile 702 is used for a combined bi-focal and tri-focal lens. In some embodiments, the apparatus 100 with the asymmetric height profile 702 is used for an anterior bifocal and a posterior tri-focal lens. In some embodiments, the apparatus 100 with the asymmetric height profile 702 is used for a posterior bifocal and an anterior tri-focal lens.

FIGS. 8 and 9 illustrate a plurality of height profiles of the angularly-varying phase member of the lens in accordance with various illustrative embodiments. As shown in FIG. 8, the height profile is symmetric at each meridian in that the maximum height (shown as 802, 804, and 806) at the face of the lens are the same. As shown in FIG. 9, the height profile is asymmetric in that the maximum height at the face of the lens are different.

Figure 10:
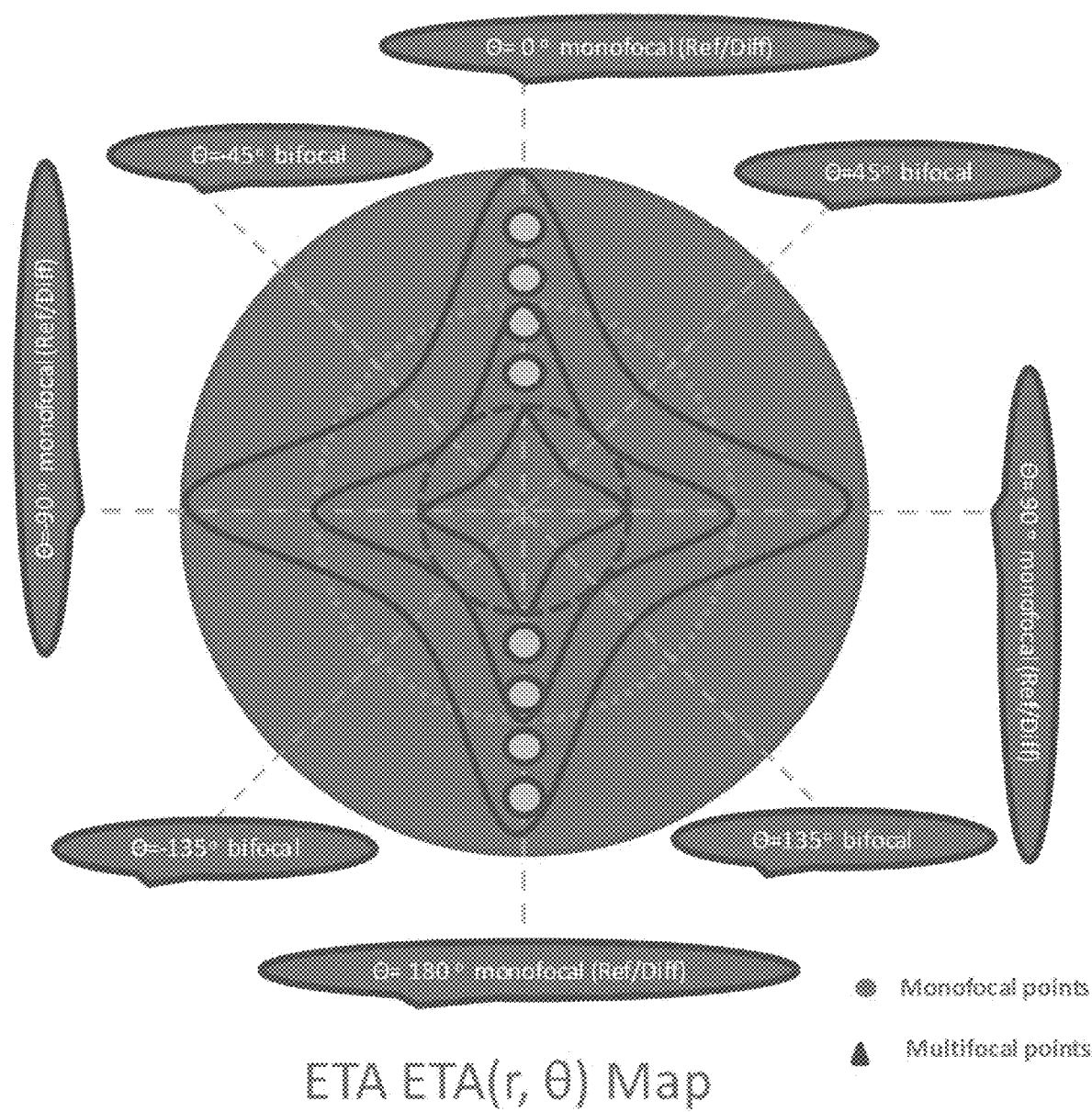
FIG. 10 is a diagram of an exemplary multi-focal lens ophthalmic apparatus that includes angularly-varying phase members in accordance with an illustrative embodiment.

FIG. 10 illustrates an example multi-focal interocular lens 1000 configured with angularly varying phase member in accordance with an illustrative embodiment. As shown, the lens 1000 provides a mono-focal at corrective meridian θ=0° and 180°. In addition, the lens 1000 provides a second mono-focal at corrective meridian θ=90° and −90°. In addition, the lens 1000 provides a first bi-focal at θ=−45° and 135°. In addition, the lens 1000 provides a second bi-focal at θ=45° and −135°. In some embodiments, the lens is refractive. In other embodiments, the lens is diffractive.

Figure 11:
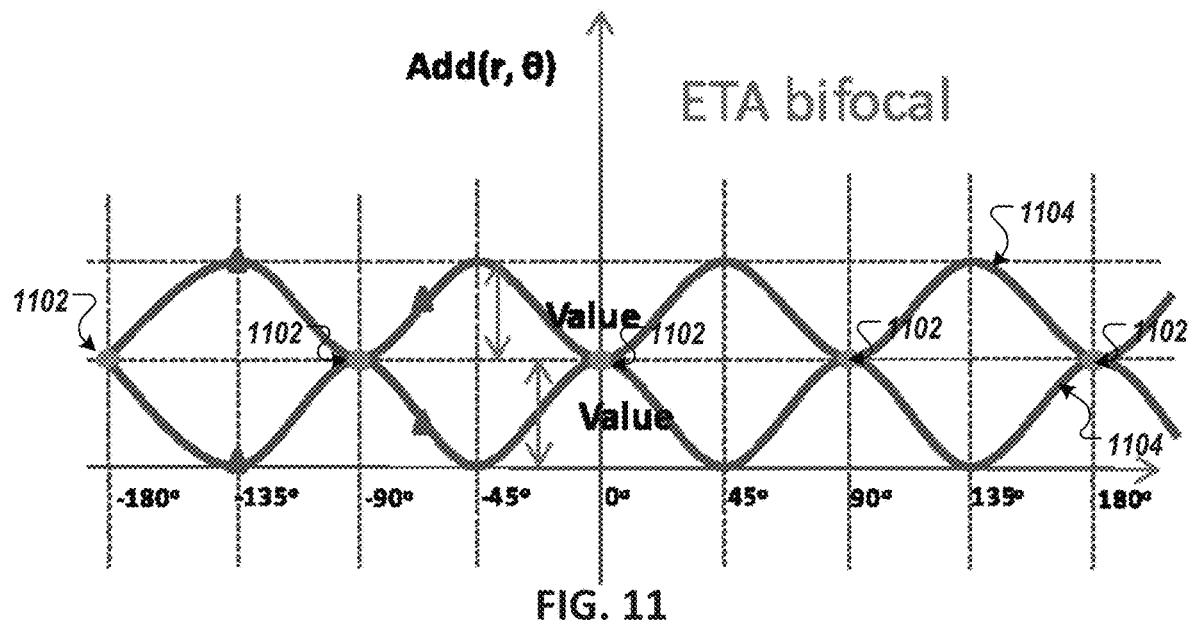
FIG. 11 is a diagram illustrating the multi-focal lens ophthalmic apparatus of FIG. 10 configured as a bifocal lens in accordance with an illustrative embodiment.
Figure 12:
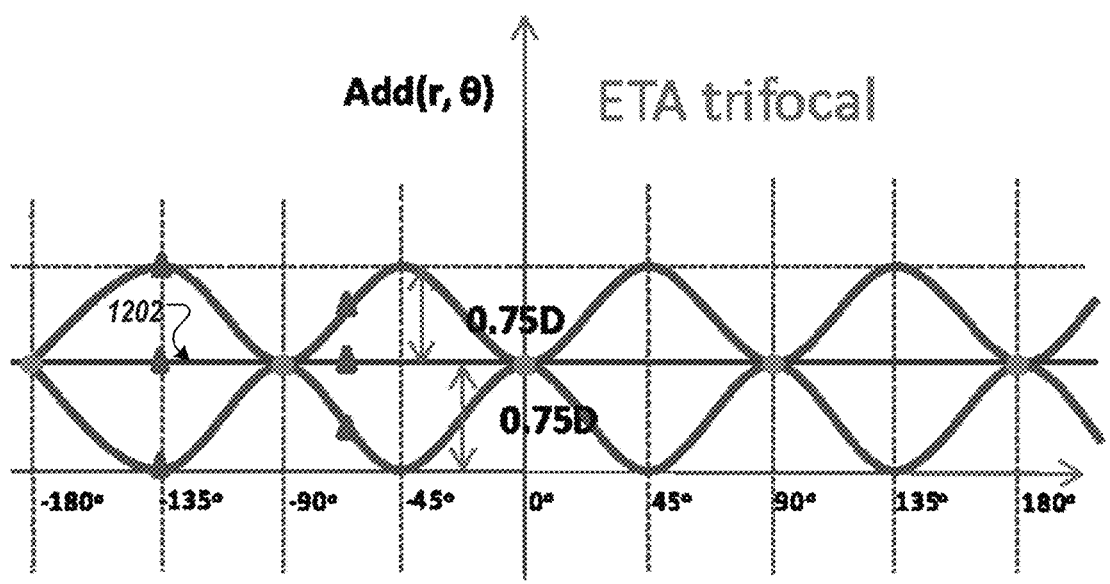
FIG. 12 is a diagram illustrating the multi-focal lens ophthalmic apparatus of FIG. 10 configured as a tri-focal lens in accordance with an illustrative embodiment.

With the angularly varying phase member, images at all meridians (θ=0°, θ=45°, θ=90°, θ=135°, θ=180°, θ=−135°, θ=−90°, and θ=−45°) reach a 20/20 uncorrected distance visual acuity (UDVA). FIGS. 11 and 12 are diagrams illustrating added cylindrical power, from the angularly varying phase members, in the radial and angular position in accordance with the illustrative embodiments.

FIG. 11 illustrates added cylinder power by the angularly varying phase member for a multi-focal interocular lens configured as a bifocal. As shown in FIG. 11, for a given cylindrical power (e.g., 6.0 Diopters), the angularly varying phase members add varying magnitude of cylinder power between the peak corrective meridian θ=0° (e.g., the astigmatic meridian) and the non-peak corrective meridian θ=45° in which minimum cylinder power is added at θ=0° (where the meridian is a mono-focal, shown at points 1102), and in which the maximum cylinder power is added at θ=45° where the meridian is configured as a bi-focal (shown along line 1104). The added power to the non-peak corrective meridian increases the tolerance of the IOL to misalignment from the corrective axis.

FIG. 12 illustrates a trifocal interocular lens with the angularly varying phase member in accordance with an illustrative embodiment. As shown in FIG. 12, the added varying cylinder power is added between the peak corrective meridian θ=0° and the non-peak corrective meridian θ=45°, as shown in FIG. 11. As further shown, a trifocal optics 1202 is added. The trifocal 1202 does not have an angularly varying phase member.

Figure 13:
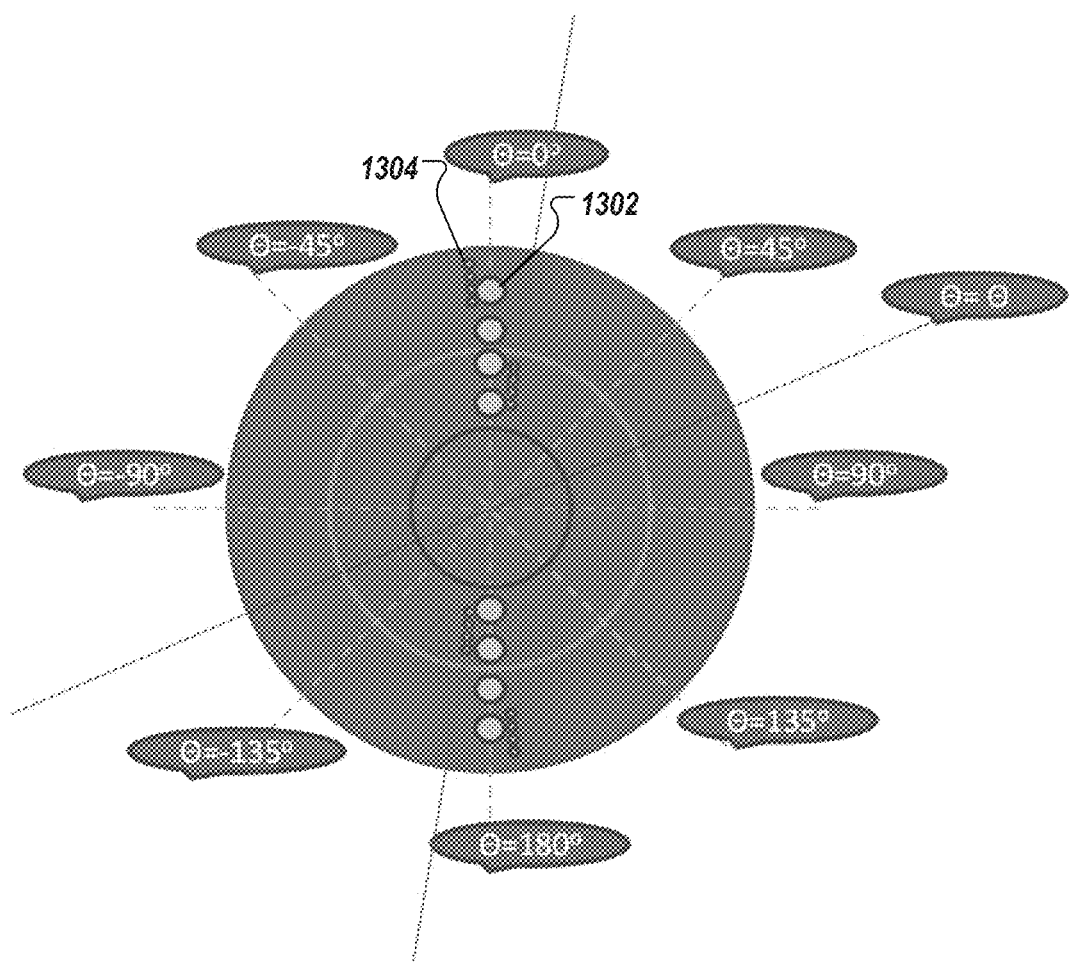
FIG. 13 is a diagram of an exemplary ophthalmic apparatus that includes angularly-varying phase members in accordance with another illustrative embodiment.

FIG. 13 illustrates an ophthalmic apparatus 1300 having angularly varying phase member to extend tolerance of ocular astigmatism by varying extended depth of focus at each meridian through an optimized combination of angularly and zonally diffractive phase structure on each meridian in accordance with an illustrative embodiment.

As shown in FIG. 13, the ophthalmic apparatus 1300 includes a first corrective meridian 90°*N°±α° (variable 01), where α is the extended tolerance of the first corrective meridian, and N is an integer. For N=0, 1, 2, 3, 4, the meridians includes 0° (1402), ±90° (1404), and 180° (1406). In some embodiments, α is ±3°, ±3.25°, ±3.5°, ±3.75°, ±4°, ±4°, ±4.25°, ±4.5°, ±4.75°, ±5°, ±5.25°, ±5.5°, ±5.75°, or ±6°. Where α is ±5°, the IOL would have a dynamic and optimized efficiency for correcting astigmatic effects that can tolerate misalignment of the cylindrical axis up to 10 (variable 08) degrees.

FIG. 14 illustrates a table for a trifocal IOL configured with the angularly varying phase member. As shown in FIG. 14, the light transmission efficiency at a first corrective foci 1402 (e.g., at the retina) is about 100% while other foci along the same meridian is about 0%. This configuration establishes the first corrective meridian 1402 at θ=0° and other meridians θ=±90° and 180°, as a monofocal with additional chromatic aberration reduction.

In addition, at meridian 45°*N°±α° (1408 and 1410) (variable 02), the light transmission efficiency varies for three point of focus (shown as 1408a, 1408b, and 1408c) (e.g., at the front of the retina, at the retina, and behind the retina) of the optics at this meridian. For N=1, 2, 3, 4, the meridians includes ±45° and ±90°. As shown in FIG. 14, at the first foci (1408a) (e.g., at the front of the retina), the light transmission efficiency is about 25% (variable 03), and the optics includes added power that matches the ocular astigmatic power corresponding to the human astigmatism tolerance level. At the second foci (1408b) (e.g., at the retina), the light transmission efficiency is about 50% (variable 04) efficiency. At the third foci (1408c) (e.g., behind the retina), the light transmission efficiency is about 25% (variable 05), and the optics include added power having the same magnitude as the first foci though with an opposite sign. At other meridians, the focus on the retina has efficiency between 0.5% and 100% (variable 06,) and the other focus not on the retina has efficiency between 0% and 25% (variable 07).

The thickness profile $T_1(r, \theta)$ for the IOL may be characterized by Equation 2 below.

$$T_1(r,\theta)=t_1(r)|\text{COS}^2(\theta)|+t_2(r)|\text{SIN}^2(\theta)| \qquad \text{(Equation 2)}$$

According to Equation 2, $t_1(r)$ and $t_2(r)$ are step heights for each zone, and they each matches an optical path difference (OPD) from 0 to 2λ, where λ is the design wavelength at zonal radius r.

FIGS. 15, 16A, 16B, 16C, 17, 18A, 18B, and 18C depict the ophthalmic apparatus with angularly varying phase members in accordance with another illustrative embodiment. According to this embodiment, the angularly varying phase member is located with a fixed-size zone and varies only along the angular position.

As shown in FIG. 15, the ophthalmic apparatus includes a plurality of zones 1502 (shown as 1502a, 1504b, and 1504c). The zones 1502a, 1502b, 1502c defined at a first corrective meridian θ=0° and 180° (1506) has approximately the same area (i.e., cylinder power) as the zones 1502a, 1502b, 1502c defined at a second meridian θ=45° and 135°. As further shown in FIGS. 16A, 16B, and 16C, the height profile (shown as 1602, 1604, 1606, 1608, 1610, and 1612) of the face of the lens varies along the angular position θ=0°, θ=9°, θ=18°, θ=27°, θ=36°, and θ=45°.

FIG. 17 illustrates ophthalmic apparatus having a height profile across the multiple zones (shown as 1702a, 1702b, and 1702c) in which the height of the face of the lens angularly varies with the meridian axes. As shown in FIGS. 18A, 18B, and 18C, the height profile (shown as 1802, 1804, 1806, 1808, 1810, and 1812) of the face of the lens varies along the angular position θ=0°, θ=9°, θ=18°, θ=27°, θ=36°, and θ=45°.

Referring back to FIG. 13, in another aspect, the ophthalmic apparatus includes a plurality of alignment markings, including a first set of alignment markings 1302 and a second set of alignment markings 1304, that indicate the corrective meridian of the lens. In some embodiments, the first set of alignment markings 1302 is located at the meridian θ=0° and 180°. The second set of alignment markings 1304 may include corresponding sets of markets to define a tolerance band for the lens. In some embodiments, the second set of alignment markings 1304 is located at ±5° radial offset from the first set of alignment markings 1302.

Figure 19A:
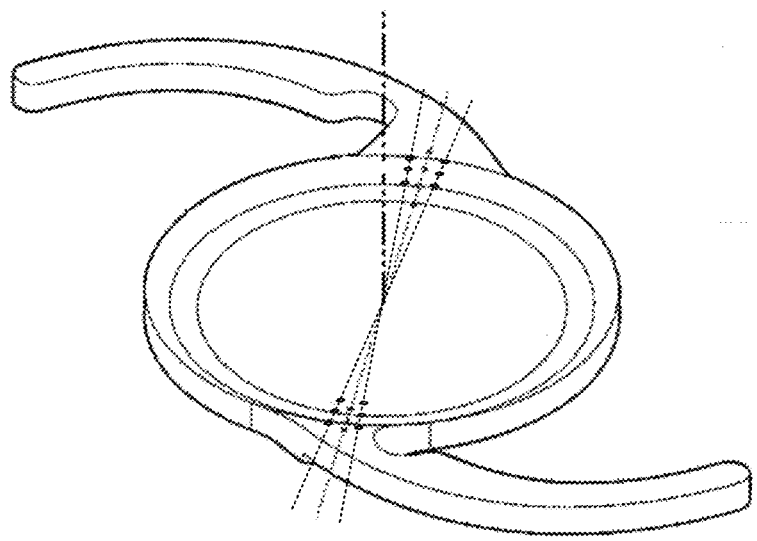
FIGS. 19A and 19B are diagrams illustrating a top and bottom view of an ophthalmic apparatus of FIG. 13 with extended tolerance band markers in accordance with an illustrative embodiment.
Figure 19B:
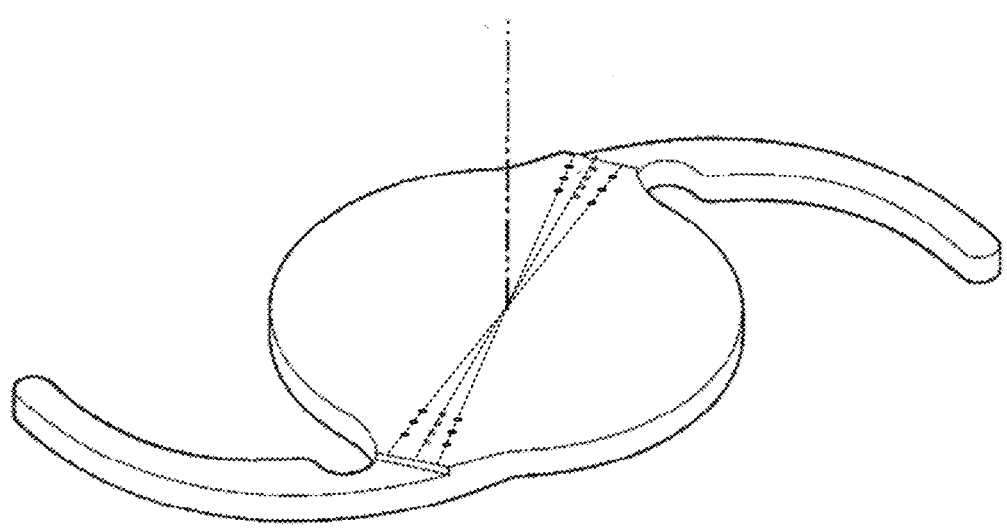

FIGS. 19A and 19B depicts an ophthalmic apparatus with an extended tolerance astigmatic band. The ophthalmic apparatus includes the second set of alignment markings 1304 as discussed in relation to FIG. 13.

The present technology may be used, for example, in the Tecnis toric intraocular lens product line as manufactured by Abbott Medical Optics, Inc. (Santa Ana, Calif.).

It is not the intention to limit the disclosure to embodiments disclosed herein. Other embodiments may be used that are within the scope and spirit of the disclosure. In some embodiments, the above disclosed angularly varying phase member may be used for multifocal toric, extended range toric, and other categorized IOLs for extended tolerance of astigmatism caused by factors including the cylindrical axis misalignment. In addition, the above disclosed angularly varying phase member may be applied to spectacle, contact lens, corneal inlay, anterior chamber IOL, or any other visual device or system.

Predicting Spherical Equivalent and Cylinder Power for ETA, ERV, and EDOF IOLs and Toric IOLs.

Definitions

"Extended Depth of Focus (EDOF) Intraocular lenses": As used herein, the terms "extended focus" or "extended depth of focus" (EDOF) include a depth of focus of a test lens, optic, or optical element that exceeds the depth of focus of a reference optic. The reference optic may have biconvex or biconcave surfaces, which may have equal radii of curvature, and an optical power or focal length that may be equal to an optical power or focal length of the test optic. The depth of focus for the test optic and the reference optic are determined under the same aperture conditions and under equivalent illumination conditions. Examples of extended depth of focus lenses are described in U.S. Publication No. 2011/0166652, filed Jul. 7, 2011, title "Toric Lens with Decreased Sensitivity to Cylinder Power and Rotation and Method of Using the Same," the text of which is incorporated by reference herein in its entirety. EDOF is attributable to a particular surface feature, structure, or mask associated with the test optic, the reference optic may be made of the same material, and have the same structure, as the test optic, except without the particular feature, structure, or mask. For example, if a test optic is a refractive or diffractive multifocal optic including a mask for extending the depth of focus of at least one of the foci formed by the test optic, then a suitable reference optic may be made of the same material(s) as the test optic and have the same structure as the test optic (e.g., surface shapes/curvatures, thickness, aperture, echelette geometry, and the like), but without the mask. The EDOF element may produce a depth of focus for each meridian. The depth of focus may indicate a good focus for each meridian at a broader range of foci. As used herein, good focus may be a focus that proves useful for vision, and that may be measured using a point spread function, defocus curves, a modulation transfer function (MTF), or by analysis of the Zernike polynomial understood to those skilled in the pertinent arts.

"Extended Range of Vision (ERV) Intraocular lens": ERV IOL are a class of IOL lenses that provide patients with a continuous range of vision including far, intermediate, and near distances with reduced incidence of halo and glare comparable to a monofocal lens. The ERV IOL is also configured to increase the distance over which an object appears in focus without sacrificing the patient's visual clarity or contrast when compared with standard monofocal IOLs that provide improved distance vision only.

"Manifest refraction spherical equivalent" (or "manifest refraction in spherical equivalent") (MRSE): is an optical examination or measurement to determine refractive error. During the examination or measurement, a patient is often asked to comparatively select from among a set of test lens, each of different refraction configurations in spherical equivalent, to which provide a better vision.

"Modulation Transfer Function" (MTF): MTF is an optical measurement of the modulation of the amplitude and phase functions of an image formed by white light on a specified plane, commonly a detector such as the retina of the human eye. MTF describes the contrast sensitivity of a lens system and may be used, for example, to predict or determine good focus, such as by simulation, and/or may be measured of the eye. MTF may be characterized as a contrast between alternating bright and dark bars in an image. A value of "1" MTF indicates that the bright bars are completely bright and dark bars are completely dark. A value of "0" MTF indicates that the bright bars and dark bars are equally gray. MTF may have a dependence on spatial frequency that is inversely related to the width of the alternating bright and dark bars in an image. Generally, an MTF may be measured using white light or may use green light, such as approximately 550 nm wavelength light. The MTF in white light can be determined using, but not limited to, theoretical modeling and calculation in an eye model, or a MTF test bench following the MTF definition; experimental lab measurement using a MTF test bench; and in-vivo measurement of a patient's eye using a diagnosis instrument.

"Spherical equivalent power" (SE): is an average dioptric power or average power for a lens. The power of a spectacle or toric lens is defined as the reciprocal of the distance from the position, for example, on the back surface of the lens where the line of sight passes through to the focal point in the eyeball. Light rays passing through the periphery of the lens, however, form a plurality of focal points due to astigmatism.

"Targeted spherical equivalent": SE targeted is the planned post-operative refractive or residual sphere equivalent of, for example, a planned cataract surgery for an eye to receive an implant. It is typically determined by a doctor with tools like a toric calculator, personalized IOL power calculator, or pre- and/or in-surgery instrument.

"White light": a spectrum of light with different wavelengths commonly visible to the human eye such as the photopic or mesopic or even scotopic light. The wavelength range typically ranges from 380 nm to 750 nm. For a UV only filtered white light, the range can be from 400 nm to 700 nm. The other filtered white light can be different. The transmission of each wavelength can be different, from 0% to 100% if normalized.

IOL Calculator

In another aspect, an IOL calculator is disclosed to determine the spherical equivalent (SE) and cylinder power for toric lenses and ophthalmic apparatuses having the extended band of operational meridian, such as the rotational extended tolerant toric intraocular lens (hereinafter "ETA toric IOL"), described herein. The IOL calculator may also be used for an extended rotational tolerant toric intraocular lens (hereinafter "ETA toric IOL"), an extended depth of field intraocular lens (hereinafter "EDOF IOL"), an extended depth of field toric intraocular lens (hereinafter "EDOF toric IOL"), an extended range of vision intraocular lens (hereinafter "ERV IOL"), and an extended range of vision toric intraocular lens (ERV toric IOL).

The exemplified IOL calculator determines a spherical equivalent and cylinder power to correctively apply to the toric lenses and ophthalmic apparatuses that beneficially minimize the residual refractive error associated therewith. The error may be minimized for both the spherical equivalent and the cylinder power.

To determine spherical equivalent and/or cylinder power that is suitable to correct, for example, for astigmatism, the IOL calculator, in some embodiments, seeks to minimize the intended corrective power for a given angle of misalignment, whereby the remaining available corrective power may be allocated to other angles of operation (i.e., at other angles of misalignment). Put another way, rather than having the cylinder power predominately converge to a given point of focus, multiple points of foci are used that are offset from the center point. As illustrated in FIGS. 5 and 6, the ETA toric IOL has a reduced peak modulation transfer function at zero degree misalignment, but maintains the performance of the lens across a range of misalignments such as up to 10 degrees. To this end, the likelihood that a supplemental corrective lens (e.g., spectacle or contact lens) or a second surgical procedure being needed can be reduced.

In an embodiment, the exemplified IOL calculator determines an initial spherical equivalent and/or cylinder power for an ophthalmic device to be used for a given eye and recursively adjusts the spherical equivalent and cylinder power to be in the range of benefit of the extended band of operational meridian. To this end, a trade-off is optimally achieved in which the expected residual refractive error is minimized, for a pre-defined range of angles of misalignment. The pre-defined range of angles may be expressed as a maximum misaligned angle expected, based on clinical data, for a class of toric lens, for example, having a given haptics or anchoring configuration. Examples of these range of angles include ±2°, ±3°, ±4°, ±5°, ±6°, ±7°, ±8°, 9° and ±10° of misalignment. In some embodiments, greater than ±10° of misalignment may be used.

Figure 20:
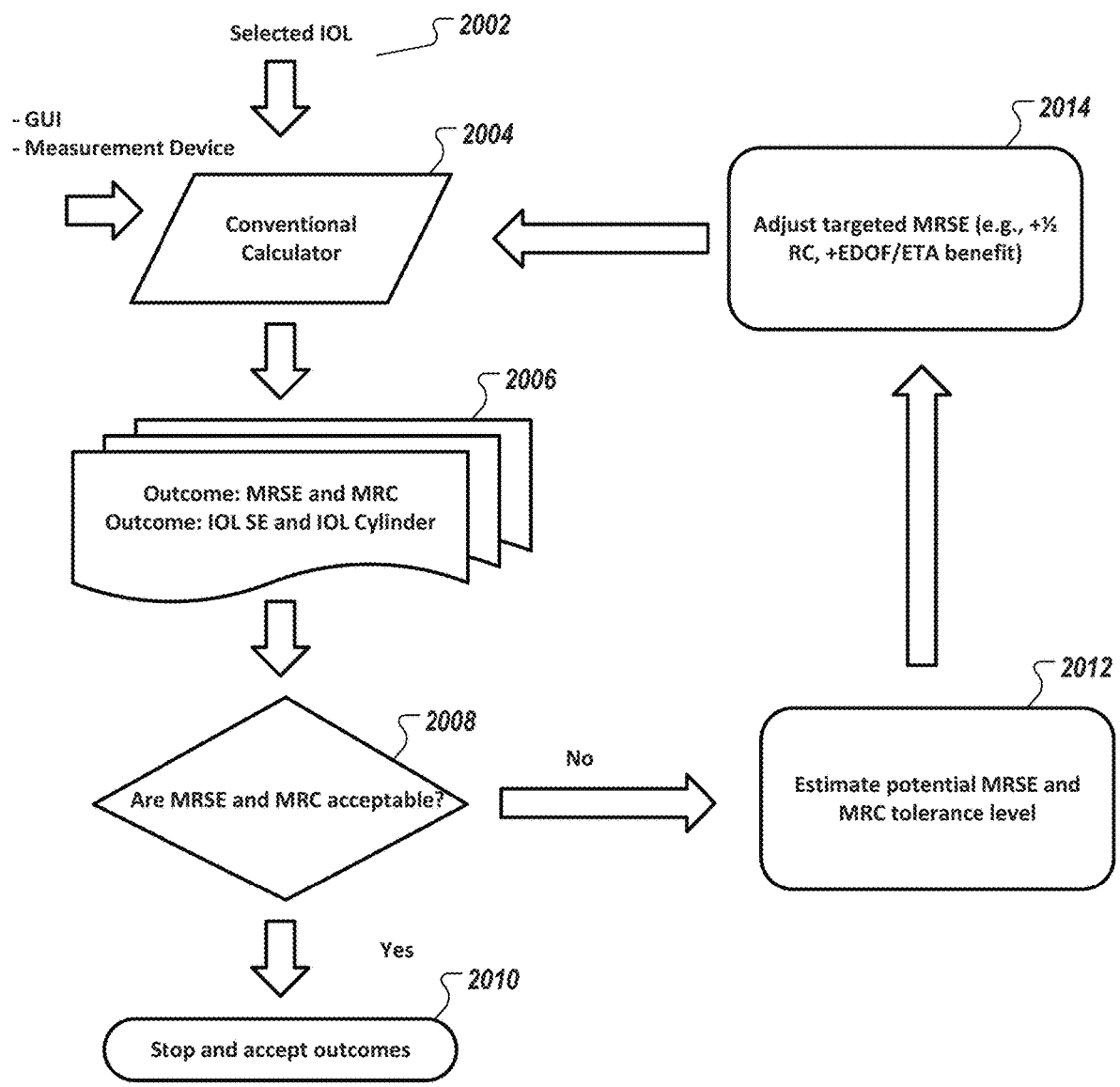
FIG. 20 is a flow chart of a method to determine the spherical equivalent (SE) and cylinder power for toric lenses and ophthalmic apparatuses having the extended band of operational meridian, an extended depth of focus, or extended range of vision, in accordance with an illustrative embodiment.

FIG. 20 is a flow chart of a method to determine the spherical equivalent (SE) and cylinder power for toric lenses and ophthalmic apparatuses having the extended band of operational meridian, an extended depth of focus, or extended range of vision.

Step 1: In a workspace that presents visual representation of a calculator, the method, in some embodiments, includes presenting a list of IOL model (e.g., ETA IOL, ERV IOL, and EDOF IOL). As shown in FIG. 20, a selection of an IOL is received along with either measurements parameters collected at a keratometry measurement device or a graphical user interface configured to receive keratometry and/or biometry information (2002), for example, from a user such as a physician or clinician.

Figure 21:
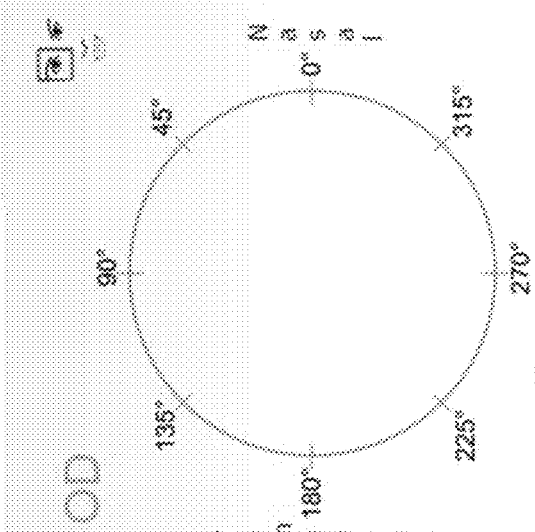
FIG. 21 illustrates an example toric calculator that can be configured to receive a selection of an IOL model in accordance with an illustrative embodiment.

FIG. 21 illustrates an example toric calculator that can be configured to receive a selection of an IOL model. Table 1 illustrates a listing of example IOL models that may be displayed for selection in the IOL calculator.

TABLE 1

| | |
|---|---|
| 1 | Extended Depth of Focus Intraocular Lens (EDOF IOL) |
| 2 | Extended Depth of Focus (EDOF) Toric Intraocular Lens (EDOF toric IOL) |
| 3 | Extended Range of Vision Intraocular Lens (ERV IOL) |
| 4 | Extended Range of Vision Toric Intraocular Lens (ERV toric IOL) |
| 5 | Extended Tolerant (Rotational) Astigmatism Intraocular Lens (ETA IOL) |
| 6 | Extended Tolerant (Rotational) Astigmatism Toric Intraocular Lens (ETA toric IOL) |

Step 2: Perform a calculation for the selected IOL model using one of known lens power calculation technique or calculator (2004). An example of an IOL calculator is the AMO Toric Calculator "Tecnis® Toric Aspheric IOL", provided by Abbott Medical Optics, Inc. (Santa Clara, Calif.) FIG. 20 illustrates a graphical user interface of an AMO Toric Calculator. The graphical user interface has inputs to receive inputs for keratometry and/or biometry data for a given patient or class of patients, to determine cylinder power and spherical equivalents for the patient (or class thereof). The output of the calculation includes spherical equivalent and cylinder power parameters (2006). In addition, the manifest refractive spherical equivalent (MRSE) and residual cylinder power (MRC) are also determined and are used to determine, for example, if the distance image is sufficient for each meridian (2008). If the MRSE and MRC are within acceptable ranges, for example, the distance image are good enough at each meridian (2008), the calculated spherical equivalent and cylinder power may be presented to the user (2010).

IOL calculators may use formulas such as Haigis L formula ("Haigis L"); the double K method with the Wang, Koch and Maloney ("DoubleK_WKM") correction; the HofferQ formula; SRK optimized formula; SRK/T formula; and the Holladay1 formula. Further descriptions of these power calculator techniques are illustrated in Table 2 and are provided, for example, in U.S. application Ser. No. 14/148, 420, title "Apparatus, System, and Method for Intraocular Lens Power Calculation Using a Regression Formula Incorporating Corneal Spherical Aberration," the text of which is incorporated by reference herein in its entirety.

TABLE 2

| | |
|---|---|
| HofferQ | P = 2.057938 + 0.944393 * HofferQ + 4.671033 |
| SRK Optimized | P = 140.8232 − 2.651 * AXL − 1.3102 * K + 4.767704 where P represents the IOL power to implant; AXL represents the axial length measured prior to the surgery; and K represents the corneal power also measured in the cataract preoperative stage. |
| SRK/T | P = 1.70056 + 0.955562 * SRK/T |
| Holladay1 | P = 2.787859 + 0.888706 * Holladay + 9.695131 |

Step 3: Predict random residual astigmatism power for the residual cylinder (2012). For a 10-degree misalignment error of astigmatism axis, in ideal case with or without SIA (surgeon induced astigmatism), the possible range of the refractive or residual cylinder (RC) can be calculated.

As discussed in relation to FIG. 4A, the residual meridian power can be expressed as Equation 1, $$OC = 2\sin\alpha * \frac{C}{2} 0.7 \cos\left(2(\theta + 90 + \frac{\alpha}{2})\right),$$

where C is the astigmatic power at the IOL plane to be corrected at meridian theta and the α is the misalignment of the cylindrical power axis. In some embodiments, for a given astigmatism power, the residual meridian power can be calculated using an expected maximum value for α. In the above example, if a given lens is designed to be tolerant up to 10 degrees of misalignment, a can be specified as 10 degrees.

In some embodiments, the random residual cylinder (RC) can be randomly selected value, for example, up to 1.5 diopters. The selection may be based on Monte Carlo simulation, or other statistically derived simulations. In other embodiments, the random residual astigmatism power can be a maximum value (such as 1.5 diopters) selected for a given intraocular designs design. In such embodiments, it should be appreciated that other powers may be selected based on the lens and the underlying pathology of the patient.

Step 4: Add ½ residual cylinder (RC) (myopia), for example, determined in Step 3, to the targeted spherical equivalent (SE) (2014). The goal is to cause, post-operatively, the far end vision of SE value+½ RC to be the distance vision. It is contemplated that other RC values may be used.

For example, for a residual cylinder of 1.5 D of a given intraocular lens, the new targeted SE can be calculated as 0+½ (1.5 D), which results in a value of 0.75 Diopters. This addition is intended to cause the image of a distant object to be clear in any meridian, when using EDOF/ETA features described herein. In some embodiments, the residual cylinder is a negative parameter (i.e., "−½RC") (e.g., for hyperopia) based on the convention used by the user.

As a further example, for a biconvex, anterior toric shaped IOL having cylinder power of 6.0 diopters at the IOL plane and 4.11 diopters at the corneal plane (e.g., Tecnis® Toric aspheric IOL, manufactured by Abbott Medical Optics, Inc. (Santa Ana, Calif.), model no. ZCT600), a 5-degree misalignment of the toric lens from the intended corrective meridian can cause a residual (refractive) of 0.75 Diopters RC and about 0.4 Diopters SE for distance vision. Because the residual cylinder is outside the range of tolerance of a healthy human eye (e.g., the astigmatism tolerance of a typical human eye is about 0.4 D at the cornea plane to produce a 20/20 vision), use of a supplemental corrective lens (such as a spectacle or contact lens) may still be needed to achieve normal visual acuity (i.e., 20/20 vision).

As yet a further example, using the toric lens that results in a refractive hyperopic of 0.4 D RC and 0.2 D SE (the SE is halved due to the lens operating outside the benefit of the ZXB00 feature), a patient may still need to need to wear supplemental eyewear (e.g., spectacle or contact lens) to have 20/20 vision or to correct for some visual effects (e.g., halo or glare) at 20/20 vision. Using the above new calculator, the calculator adds 0.2 D SE+0.4/2 RC=0.4 D to the targeted SE and re-run the calculation. The result, in this example, will be 0.2 D RC with −0.4 D SE.

Using these modifications for the ETA, ERV, or EDOF IOLs or toric IOLs, and following the validation of parameters (such as manifest refraction spherical equivalent and manifest residual cylinder) being within the benefit of the ZXT600 feature and well within the astigmatism tolerance range of the human eye, the need for supplemental corrective lens or additional corrective surgical procedures can be substantially reduced.

Step 5: Re-run the calculation and add the residual refraction through focus and meridian three-dimensional flow (e.g., 2014, 2004, and 2008). In some embodiments, this has the effect of providing an enhanced modulation transfer function through focus and additional through meridian at each focus plane. That is, after the update to the targeted SE, the corresponding other residuals (refractions) can be again simulated and calculated at each meridian at a position focused, at the positions in the front (myopia) of the focused position, which can be combined to generate the through focus and meridian refractions.

The corresponding MTFs, in some embodiments, are the through focus and meridian MTFs. The through focus positions can be represented by the visual object in the interested distance, manifest refractions, or image focus positions relative to the retina. The through focus performance can be represented by the MTF values at a given spatial frequency or a contrast or VA (simulated). This is the method of referred to as "3D flow."

Step 6: Heighted the designed feature or benefit in the above range. That is, adjust the height profile of the lens (e.g., the lens height profile for a given angular phase member), for example, for a given zone.

Step 7: Output the spherical equivalent and power cylinder if all the powers at each meridians are in an acceptable ranges for the defined set of distance (2010). In some embodiments, the manifest refraction spherical equivalent (MRSE) parameter and/or manifest residual cylinder (MRC) are calculated by using, for example, a conventional clinic VA letter chart test with trial glasses.

Step 8: If all the powers at meridians are not in the desired range (e.g., as determined in Step 7) (2008), add residual cylinder power and repeat Steps 5-8.

The use of minimum added power (so more cylinder can be used for the extended range of operation) allows the toric lenses and ophthalmic apparatuses to operate both in range of the IOL benefit—thereby potentially minimizing the residual refractive error, including SE and cylinder power—and maximizing the spectacle or contact lenses (CL) independence. In addition, the benefits of the ETA IOL and ETA toric IOL as described in FIGS. 5 and 6 can be maximally realized with intended post-operation vision achieving the uncorrected visual acuity of 20/20 vision.

With slight modifications, the above disclosed new solutions can also be used for power calculations for multifocal toric, extended range toric, or other categorized IOLs for extended tolerance of astigmatism caused by factors including the cylindrical axis mi-alignment With slight modification, the above mentioned solution can also be applied to power calculation for spectacle, contact lens, corneal inlay, anterior chamber IOL, or any other visual device or system.

Exemplary Computer System

Figure 22:
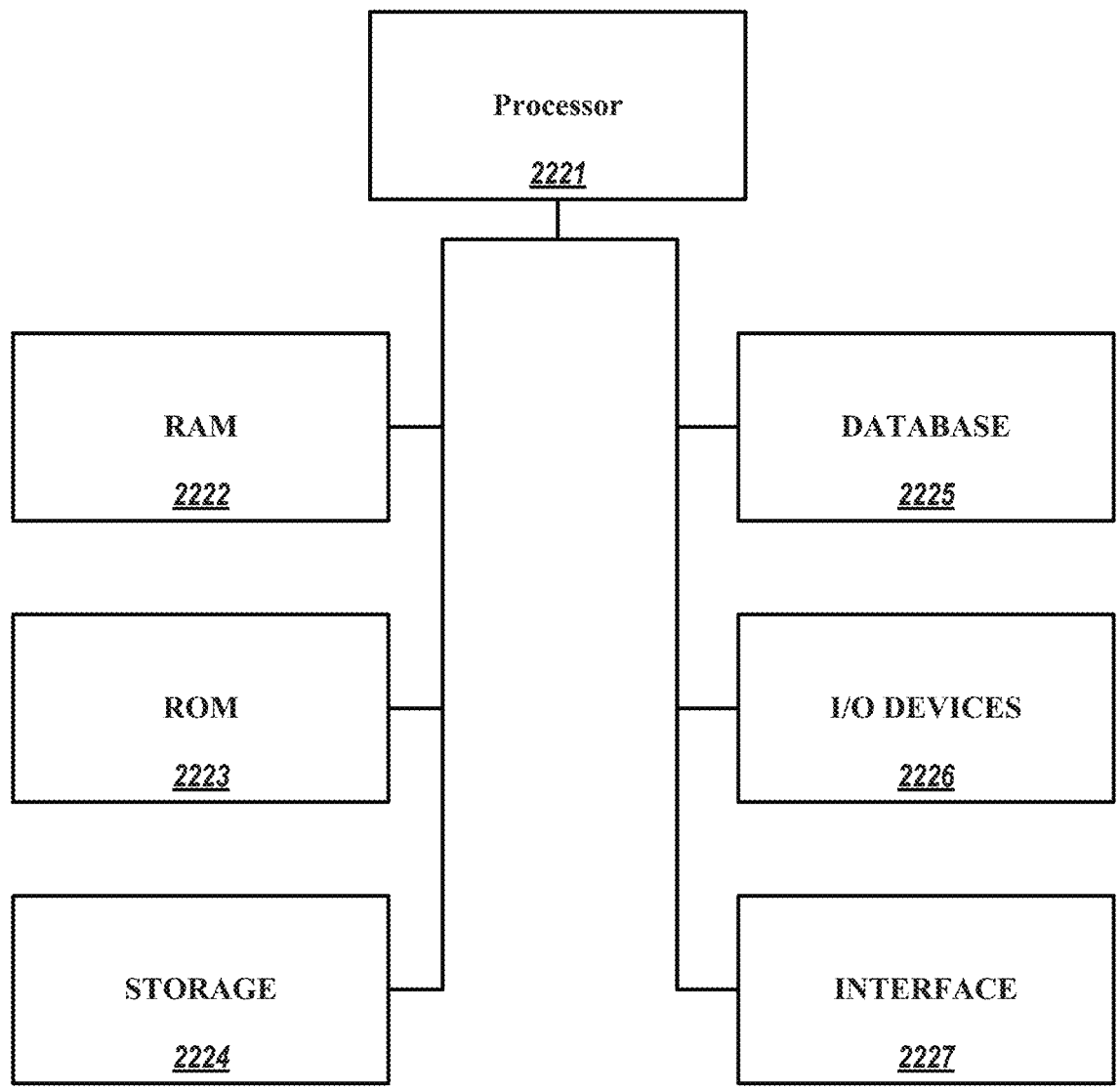
FIG. 22 illustrates an exemplary computer that can be used determining optical configuration (e.g. IOL spherical equivalent and cylinder power) of a rotationally-extended tolerant ophthalmic apparatus for the selection thereof.

FIG. 22 illustrates an exemplary computer that can be used for determining optical configuration (e.g. IOL spherical equivalent and cylinder power) of a rotationally-extended tolerant ophthalmic apparatus for the selection thereof. In various aspects, the computer of FIG. 22 may comprise all or a portion of the IOL calculator, as described herein. As used herein, "computer" may include a plurality of computers. The computers may include one or more hardware components such as, for example, a processor 2221, a random access memory (RAM) module 2222, a read-only memory (ROM) module 2223, a storage 2224, a database 2225, one or more input/output (I/O) devices 2226, and an interface 2227. Alternatively and/or additionally, controller 2220 may include one or more software components such as, for example, a computer-readable medium including computer executable instructions for performing a method associated with the exemplary embodiments. It is contemplated that one or more of the hardware components listed above may be implemented using software. For example, storage 2224 may include a software partition associated with one or more other hardware components. It is understood that the components listed above are exemplary only and not intended to be limiting.

Processor 2221 may include one or more processors, each configured to execute instructions and process data to perform one or more functions associated with a computer for indexing images. Processor 2221 may be communicatively coupled to RAM 2222, ROM 2223, storage 2224, database 2225, I/O devices 2226, and interface 2227. Processor 2221 may be configured to execute sequences of computer program instructions to perform various processes. The computer program instructions may be loaded into RAM 2222 for execution by processor 2221. As used herein, processor refers to a physical hardware device that executes encoded instructions for performing functions on inputs and creating outputs.

RAM 2222 and ROM 2223 may each include one or more devices for storing information associated with operation of processor 2221. For example, ROM 2223 may include a memory device configured to access and store information associated with controller 2220, including information associated with IOL lenses and their parameters. RAM 2222 may include a memory device for storing data associated with one or more operations of processor 2221. For example, ROM 2223 may load instructions into RAM 2222 for execution by processor 2221.

Storage 2224 may include any type of mass storage device configured to store information that processor 2221 may need to perform processes consistent with the disclosed embodiments. For example, storage 2224 may include one or more magnetic and/or optical disk devices, such as hard drives, CD-ROMs, DVD-ROMs, or any other type of mass media device.

Database 2225 may include one or more software and/or hardware components that cooperate to store, organize, sort, filter, and/or arrange data used by controller 2220 and/or processor 2221. For example, database 2225 may store hardware and/or software configuration data associated with input-output hardware devices and controllers, as described herein. It is contemplated that database 2225 may store additional and/or different information than that listed above.

I/O devices 2226 may include one or more components configured to communicate information with a user associated with controller 2220. For example, I/O devices may include a console with an integrated keyboard and mouse to allow a user to maintain a database of images, update associations, and access digital content. I/O devices 2226 may also include a display including a graphical user interface (GUI) for outputting information on a monitor. I/O devices 2226 may also include peripheral devices such as, for example, a printer for printing information associated with controller 2220, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 2227 may include one or more components configured to transmit and receive data via a communication network, such as the Internet, a local area network, a workstation peer-to-peer network, a direct link network, a wireless network, or any other suitable communication platform. For example, interface 2227 may include one or more modulators, demodulators, multiplexers, demultiplexers, network communication devices, wireless devices, antennas, modems, and any other type of device configured to enable data communication via a communication network.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations.

What is claimed is:

1. A method for determining optical configuration of an implantable ophthalmic apparatus for the selection thereof to correct an astigmatism of a patient, the method comprising:
    receiving, by a processor, measurement data associated with an eye of the patient;
    determining, by the processor, using the measurement data, an initial optical configuration of an implantable ophthalmic apparatus to apply at a corrective meridian of the implantable ophthalmic apparatus to correct the astigmatism of the patient, wherein the implantable ophthalmic apparatus comprises an extended-depth-of focus (EDOF) feature, an extended-range-of-vision (ERV) feature, or an extended-tolerant-astigmatism (ETA) feature, wherein the implantable ophthalmic apparatus is configured with an established band of operational meridian across a range from 5 degrees to 10 degrees, and wherein the initial optical configuration comprises a spherical equivalent value and cylinder power value;
    determining, by the processor, a residual cylinder (RC) power associated with a random residual astigmatism power for the implantable ophthalmic apparatus, wherein the random residual astigmatism power is associated with a rotational misalignment applied to the implantable ophthalmic apparatus following implantation of the implantable ophthalmic apparatus in the eye of the patient, wherein the random residual astigmatism power is determined at a pre-defined maximum rotational misalignment value designated for the implantable ophthalmic apparatus, wherein the random residual astigmatism power is determined based on an equation defining undesired meridian power resulting from a rotational misalignment of the implantable ophthalmic apparatus at a rotational misalignment range selected from a group consisting of ±5°, ±6°, ±7°, ±8°, ±9° and ±10°, and wherein the equation is defined as a function of at least, an angle of the rotational misalignment;

modifying, by the processor, the initial optical configuration based on the determined residual cylinder (RC) power to generate a modified optical configuration having included an adjusted spherical equivalent value or adjusted cylinder power value, wherein the modified optical configuration corrects for the undesired meridian power resulting from the rotational misalignment;

determining, by the processor, a predicted manifest refraction spherical equivalent (MRSE) data set and/or a predicted manifest residual cylinder (MRC) data set for the implantable ophthalmic apparatus configured with the modified optical configuration with the adjusted spherical equivalent value or cylinder power value;

determining, by the processor, the predicted manifest refraction spherical equivalent (MRSE) and/or the predicted manifest residual cylinder (MRC) data set being outside a pre-defined range for each meridian;

modifying, by the processor, the modified optical configuration with an adjustment value to the adjusted spherical equivalent value or cylinder power value, wherein the adjustment value is derived from the determined residual cylinder (RC) until the manifest refraction spherical equivalent (MRSE) data set or and/or the manifest residual cylinder (MRC) data set associated with the adjustment are within the pre-defined range for each meridian; and causing, by the processor, a visual representation of the re-adjusted spherical equivalent value and cylinder power value, wherein spherical equivalent and cylinder power values are used for the selection and the configuring of the implantable ophthalmic apparatus to be implanted into the eye of the patient.

2. The method of claim 1, wherein the implantable ophthalmic apparatus is selected from the group consisting of an extended tolerant astigmatism toric intraocular (ETA toric IOL) apparatus, an implantable extended tolerant astigmatism intraocular (ETA IOL) apparatus, an implantable extended-range-of-vision toric intraocular (ERV toric IOL) apparatus, an implantable extended-range-of-vision intraocular (ERV IOL) apparatus, an implantable extended-depth-of-focus toric intraocular (EDOF toric IOL) apparatus, and an implantable extended-depth-of-focus intraocular (EDOF IOL) apparatus.

3. The method of claim 1, wherein the equation defining the undesired meridian power resulting from the rotational misalignment used to determine the random residual astigmatism power is calculated as:

$$2\sin\alpha * \frac{C}{2} 0.7 \cos\left(2(\theta + 90 + \frac{\alpha}{2})\right),$$

wherein θ is the corrective meridian expressed in degrees; C is an astigmatic corrective power at the IOL plane to be corrected at the corrective meridian θ expressed in Diopters; and α is a magnitude of rotational misalignment of the cylindrical power axis to the astigmatic axis, expressed in degrees.

4. The method of claim 1, wherein the step of modifying the initial optical configuration based on the determined residual cylinder (RC) power comprises adding a value associated with the determined residual cylinder (RC) power to the spherical equivalent of the initial optical configuration.

5. The method of claim 1, wherein the extended-depth-of-focus (EDOF) feature or the extended-tolerant-astigmatism (ETA) feature of the implantable ophthalmic apparatus comprises a combination of angularly and zonally refractive or diffractive phase structure located at the corrective meridian, the phase structure being configured to vary an extended depth of focus of nearby focus points located near the corrective meridian such that rotational offset from the corrective meridian directs light from the nearby focus points to a point of focus of the corrective meridian, thereby establishing an extended band of operational meridians over the corrective meridian.

6. The method of claim 1, wherein the initial optical configuration is determined using a power calculator configured with a formula selected from the group consisting Hoffer Q formula, SRK optimized formula, SRK/T formula, and Holladay I formula.

7. A non-transitory computer readable medium, the computer readable medium having instructions stored thereon, wherein the instructions, when executed by a processor, cause the processor to:

receive measurement data associated with an eye of a patient;

determine, using a power calculator and the measurement data, an initial optical configuration of an implantable ophthalmic apparatus to apply at a corrective meridian of the implantable ophthalmic apparatus to correct the astigmatism of the patient, wherein the implantable ophthalmic apparatus comprises an extended-depth-of-focus (EDOF) feature, an extended-range-of-vision (ERV) feature, or an extended-tolerant-astigmatism (ETA) feature, wherein the implantable ophthalmic apparatus is configured with an established band of operational meridian across a range from 5 degrees to 10 degrees, and wherein the initial optical configuration comprises a spherical equivalent value and cylinder power value;

determine a random residual astigmatism power as a residual cylinder (RC) power for the implantable ophthalmic apparatus, wherein the random residual astigmatism power is associated with a rotational misalignment applied to the implantable ophthalmic apparatus following implantation of the implantable ophthalmic apparatus in an eye of the patient, wherein the random residual astigmatism power is determined at a pre-defined maximum rotational misalignment value designated for the implantable ophthalmic apparatus, wherein the random residual astigmatism power is determined based on an equation defining undesired meridian power resulting from a rotational misalignment of the implantable ophthalmic apparatus at a rotational misalignment range selected from a group consisting of ±5°, ±6°, ±7°, ±8°, ±9° and ±10°, and wherein the equation is defined as a function of at least, an angle of the rotational misalignment;

modify the initial optical configuration based on the determined residual cylinder (RC) power to generate a modified optical configuration having included an adjusted spherical equivalent value or adjusted cylinder power value, wherein the modified optical configuration corrects for the undesired meridian power resulting from the rotational misalignment;

determine a predicted manifest refraction spherical equivalent (MRSE) data set and/or a predicted manifest residual cylinder (MRC) data set for the implantable ophthalmic apparatus configured with the modified optical configuration with the adjusted spherical equivalent value or cylinder power value:

determine the predicted manifest refraction spherical equivalent (MRSE) data set and/or the predicted manifest residual cylinder (MRC) data set being outside a pre-defined range for each meridian:

modify the modified optical configuration with an adjustment value to the adjusted spherical equivalent value or cylinder power value, wherein the adjustment value is derived from the determined residual cylinder (RC) until the manifest refraction spherical equivalent (MRSE) data set and/or the manifest residual cylinder (MRC) data set are within the pre-defined range for each meridian:

and cause a visual representation of the re-adjusted spherical equivalent value and cylinder power value, wherein the presented readjusted spherical equivalent and cylinder power values are used for the selection and the configuring of the implantable ophthalmic apparatus to be implanted into the eye of the patient.

8. The computer readable medium of claim 7, wherein the implantable ophthalmic apparatus is selected from the group consisting of an extended tolerant astigmatism toric intraocular (ETA toric IOL) apparatus, an implantable extended tolerant astigmatism intraocular (ETA IOL) apparatus, an implantable extended-range-of-vision toric intraocular (ERV toric IOL) apparatus, an implantable extended-range-of-vision intraocular (ERV IOL) apparatus, an implantable extended-depth-of-focus toric intraocular (EDOF toric IOL) apparatus, and an implantable extended-depth-of-focus intraocular (EDOF IOL) apparatus.

9. The computer readable medium of claim 7, wherein the equation defining the undesired meridian power resulting from the rotational misalignment used to determine the random residual astigmatism power is calculated as:

$$2 \sin \alpha * \frac{C}{2} 0.7 \cos\left(2\left(\theta + 90 + \frac{\alpha}{2}\right)\right),$$

wherein $\theta$ is the corrective meridian expressed in degrees; C is an astigmatic corrective power at the IOL plane to be corrected at the corrective meridian $\theta$ expressed in Diopters; and $\alpha$ is a magnitude of rotational misalignment of the cylindrical power axis to the astigmatic axis, expressed in degrees.

10. The computer readable medium of claim 7, wherein the instructions that performs the step to modify the initial optical configuration based on the determined residual cylinder (RC) power performs said step by adding a value associated with the determined residual cylinder (RC) power to the spherical equivalent of the initial optical configuration.

11. The computer readable medium of claim 7, wherein the equation defining the undesired meridian power resulting from the rotational misalignment of the implantable ophthalmic apparatus comprises a sinusoidal term of the angle of the rotational misalignment.

* * * * *